US009492624B2

(12) United States Patent
Faries, Jr. et al.

(10) Patent No.: US 9,492,624 B2
(45) Date of Patent: Nov. 15, 2016

(54) METHOD AND APPARATUS FOR HEATING SOLUTIONS WITHIN INTRAVENOUS LINES TO DESIRED TEMPERATURES DURING INFUSION

(75) Inventors: Durward I. Faries, Jr., Las Vegas, NV (US);
(Continued)

(73) Assignee: Medical Solutions, Inc., Chantilly, VA (US)

(*) Notice: Subject to any disclaimer, the term of this patent is extended or adjusted under 35 U.S.C. 154(b) by 296 days.

(21) Appl. No.: 13/289,213

(22) Filed: Nov. 4, 2011

(65) Prior Publication Data
US 2012/0053518 A1    Mar. 1, 2012

Related U.S. Application Data

(63) Continuation of application No. 10/016,128, filed on Dec. 17, 2001, now Pat. No. 8,226,605.

(51) Int. Cl.
*A61M 5/44* (2006.01)
*A61M 5/14* (2006.01)

(52) U.S. Cl.
CPC .............. *A61M 5/44* (2013.01); *A61M 5/1415* (2013.01); *A61M 2205/14* (2013.01); *A61M 2205/3368* (2013.01); *A61M 2205/3653* (2013.01)

(58) Field of Classification Search
CPC ................. A61M 5/44; A61M 5/1415; A61M 2205/14; A61M 2205/3368; A61M
(Continued)

(56) References Cited

U.S. PATENT DOCUMENTS

| 522,866 A | 7/1894 | Weinhagen et al. |
|---|---|---|
| 558,979 A | 4/1896 | Noble |

(Continued)

FOREIGN PATENT DOCUMENTS

| DE | 3709122 A1 | 8/1988 |
|---|---|---|
| DE | 3742927 A1 | 7/1989 |

(Continued)

OTHER PUBLICATIONS

Health Devices, vol. 25, No. 10, Oct. 1996.
(Continued)

*Primary Examiner* — Aarti B Berdichevsky
*Assistant Examiner* — Laura Schell
(74) *Attorney, Agent, or Firm* — Edell, Shapiro & Finnan, LLC

(57) ABSTRACT

An IV line temperature controlled warming device includes a housing and a fluid cassette or cartridge that receives fluid from an IV line and includes intravenous line tubing arranged in a preformed configuration. The configuration includes tubing sections arranged in generally circular and concentric portions and a central serpentine tubing section that basically reverses fluid flow and facilitates flow in opposing directions within adjacent tubing sections. The fluid cassette is retained within the device on a base plate partially disposed within a device housing interior, while a housing cover is selectively opened and closed to permit access to the base plate. The base plate includes a heater plate disposed thereon, while the cover and heater plate each include heating elements to apply heat to opposing surfaces of the tubing cassette. The heating elements are controlled by a controller in response to measured temperatures of the heater plate and fluid.

12 Claims, 6 Drawing Sheets

(75) Inventors: Bruce R. Heymann, Vienna, VA (US);
Calvin Blankenship, Frostburg, MD
(US); David Hendrix, Ashburn, VA
(US)

(58) Field of Classification Search
CPC .................. 2205/3653;A61M 2205/36; A61M
2205/3633; A61M 2205/3613; A61M
2205/362; A61M 2205/3626; A61M
2205/364; A61M 2205/3646; A61M
2205/366; A61M 2205/3673; A61M
2205/3686; A61M 2205/3693; A61M
5/445; A61M 2205/6018; A61M
2205/6027; F24H 1/06; F24H 11/121;
F24H 1/0018
USPC ................................................ 604/113, 114
See application file for complete search history.

(56) References Cited

U.S. PATENT DOCUMENTS

| | | |
|---|---|---|
| 675,647 A | 6/1901 | Andersen et al. |
| 785,524 A | 3/1905 | Shea |
| 803,352 A | 10/1905 | Meyer |
| 1,062,111 A | 5/1913 | Nylander |
| 1,092,643 A | 4/1914 | Goolsby |
| 1,110,919 A | 9/1914 | Gamble |
| 1,223,274 A | 4/1917 | Hallock |
| 1,390,500 A | 9/1921 | Christian |
| 1,479,451 A | 1/1924 | Buckstein |
| 1,493,450 A | 5/1924 | Richardson |
| 1,726,212 A | 8/1929 | Bucky |
| 1,770,832 A | 7/1930 | Bass |
| 1,794,215 A | 2/1931 | Titus |
| 1,838,026 A | 12/1931 | Williams |
| 1,847,573 A | 3/1932 | Rupp |
| 1,847,954 A | 3/1932 | Fisher |
| 1,960,417 A | 5/1934 | Pain, Jr. |
| 1,982,213 A | 11/1934 | Hopkins |
| 1,987,119 A | 1/1935 | Long |
| 1,995,302 A | 3/1935 | Goldstein |
| 2,063,902 A | 12/1936 | Beasley |
| 2,087,586 A | 7/1937 | Tishman |
| 2,124,293 A | 7/1938 | Goldstein |
| 2,204,764 A | 6/1940 | Mayo |
| 2,254,994 A | 9/1941 | Butland |
| 2,357,692 A | 9/1944 | Saffady |
| 2,470,481 A | 5/1949 | Freeman |
| 2,701,789 A | 2/1955 | White |
| 2,766,907 A | 10/1956 | Wallace, Jr. |
| 2,880,764 A | 4/1959 | Pelavin |
| 2,910,981 A | 11/1959 | Wilson et al. |
| 2,990,875 A | 7/1961 | Samuels et al. |
| 3,140,716 A | 7/1964 | Harrison et al. |
| 3,157,727 A | 11/1964 | Hardy et al. |
| 3,247,851 A | 4/1966 | Seibert |
| 3,293,868 A * | 12/1966 | Gonzalez .......................... 62/3.1 |
| 3,370,153 A | 2/1968 | Du Fresne et al. |
| 3,475,590 A | 10/1969 | Pins |
| 3,485,245 A | 12/1969 | Lahr et al. |
| 3,500,366 A | 3/1970 | Chesney et al. |
| 3,526,134 A | 9/1970 | Schaus |
| 3,551,641 A | 12/1970 | Truhan |
| 3,563,090 A | 2/1971 | Deltour |
| 3,590,215 A | 6/1971 | Anderson et al. |
| 3,591,290 A | 7/1971 | Zinner et al. |
| 3,596,515 A | 8/1971 | Cramer |
| 3,612,059 A | 10/1971 | Ersek |
| 3,614,385 A | 10/1971 | Horstmann |
| 3,629,552 A | 12/1971 | Edging |
| 3,636,767 A | 1/1972 | Duffy |
| 3,640,277 A | 2/1972 | Adelberg |
| 3,651,695 A | 3/1972 | Brown |
| 3,801,278 A | 4/1974 | Wagner et al. |
| 3,845,661 A | 11/1974 | Hollweck et al. |
| 3,864,976 A | 2/1975 | Parker |
| 3,879,171 A | 4/1975 | Tulis |
| 3,895,741 A | 7/1975 | Nugent |
| 3,908,652 A | 9/1975 | Weissinger |
| 3,940,742 A | 2/1976 | Hudspeth et al. |
| 4,009,615 A | 3/1977 | Ruhl |
| 4,024,377 A | 5/1977 | Henke |
| 4,038,519 A | 7/1977 | Foucras |
| 4,063,551 A | 12/1977 | Sweeney |
| 4,084,080 A | 4/1978 | McMahan |
| 4,090,514 A | 5/1978 | Hinck et al. |
| 4,098,123 A | 7/1978 | Granzow, Jr. |
| 4,121,574 A | 10/1978 | Lester |
| 4,138,890 A | 2/1979 | Brown |
| 4,167,663 A | 9/1979 | Granzow, Jr. et al. |
| 4,187,847 A | 2/1980 | Loeser |
| 4,189,995 A | 2/1980 | Lohr et al. |
| 4,233,495 A | 11/1980 | Scoville et al. |
| 4,293,762 A | 10/1981 | Ogawa |
| 4,309,592 A | 1/1982 | Le Boeuf |
| 4,314,484 A | 2/1982 | Bowman |
| 4,318,276 A | 3/1982 | Sato et al. |
| 4,328,676 A | 5/1982 | Reed |
| 4,329,569 A | 5/1982 | Hjortsberg et al. |
| 4,331,859 A | 5/1982 | Thomas et al. |
| 4,336,435 A | 6/1982 | Kashyap et al. |
| 4,356,383 A | 10/1982 | Dahlberg |
| 4,364,234 A | 12/1982 | Reed |
| 4,375,813 A | 3/1983 | Hessel |
| 4,384,578 A | 5/1983 | Winkler |
| 4,397,648 A | 8/1983 | Knute |
| 4,407,133 A | 10/1983 | Edmonson |
| 4,408,905 A | 10/1983 | Ehrenkranz |
| 4,419,568 A | 12/1983 | VanOverloop |
| 4,430,077 A | 2/1984 | Mittleman et al. |
| 4,430,078 A | 2/1984 | Sprague |
| 4,432,761 A | 2/1984 | Dawe |
| 4,448,204 A | 5/1984 | Lichtenstein |
| 4,455,478 A | 6/1984 | Guibert |
| 4,464,563 A | 8/1984 | Jewett |
| 4,468,137 A | 8/1984 | Hilsum et al. |
| 4,476,877 A | 10/1984 | Barker |
| 4,481,410 A | 11/1984 | Bortnick |
| 4,490,884 A | 1/1985 | Vickers |
| 4,495,402 A | 1/1985 | Burdick et al. |
| 4,498,901 A | 2/1985 | Finch |
| 4,509,532 A | 4/1985 | DeVries |
| 4,509,943 A | 4/1985 | Hanzawa |
| 4,522,308 A | 6/1985 | Sullivan |
| 4,523,078 A | 6/1985 | Lehmann |
| 4,529,309 A | 7/1985 | Pettersson et al. |
| 4,531,941 A | 7/1985 | Zasuwa |
| 4,532,414 A | 7/1985 | Shah et al. |
| 4,533,350 A | 8/1985 | Danby et al. |
| 4,543,095 A | 9/1985 | Jensen |
| 4,551,136 A | 11/1985 | Mandl |
| 4,552,277 A | 11/1985 | Richardson et al. |
| 4,572,536 A | 2/1986 | Doughty |
| 4,585,441 A | 4/1986 | Archibald |
| 4,586,691 A | 5/1986 | Kozlow |
| 4,605,840 A | 8/1986 | Koopman |
| 4,613,327 A | 9/1986 | Tegrarian et al. |
| 4,614,514 A | 9/1986 | Carr et al. |
| 4,625,086 A | 11/1986 | Karino |
| 4,626,243 A | 12/1986 | Singh et al. |
| 4,628,186 A | 12/1986 | Bergemann et al. |
| 4,634,432 A | 1/1987 | Kocak |
| 4,647,756 A | 3/1987 | Willis |
| 4,651,813 A | 3/1987 | Witt et al. |
| 4,657,004 A | 4/1987 | Coffey |
| 4,673,820 A | 6/1987 | Karmen |
| 4,674,977 A | 6/1987 | Hoselton |
| 4,678,460 A | 7/1987 | Rosner |
| 4,680,445 A | 7/1987 | Ogawa |
| 4,680,977 A | 7/1987 | Conero et al. |
| 4,682,979 A | 7/1987 | Girouard |
| 4,684,367 A | 8/1987 | Schaffer et al. |
| 4,705,505 A | 11/1987 | Fried |
| 4,707,587 A | 11/1987 | Greenblatt |

(56) References Cited

U.S. PATENT DOCUMENTS

| | | |
|---|---|---|
| 4,709,135 A | 11/1987 | Dietrich et al. |
| 4,718,896 A | 1/1988 | Arndt et al. |
| 4,726,193 A | 2/1988 | Burke et al. |
| 4,735,609 A | 4/1988 | Comeau et al. |
| 4,745,248 A | 5/1988 | Hayes |
| 4,747,450 A * | 5/1988 | Ikegame .................. F28D 7/04 165/168 |
| 4,747,826 A | 5/1988 | Sassano |
| 4,756,299 A | 7/1988 | Podella |
| 4,759,749 A | 7/1988 | Verkaart |
| 4,772,778 A | 9/1988 | Ogawa |
| 4,781,548 A | 11/1988 | Alderson et al. |
| 4,782,212 A | 11/1988 | Bakke |
| 4,801,777 A | 1/1989 | Auerbach |
| 4,804,367 A | 2/1989 | Smith et al. |
| 4,808,159 A | 2/1989 | Wilson |
| 4,823,554 A | 4/1989 | Trachtenberg et al. |
| 4,823,833 A | 4/1989 | Hogan et al. |
| 4,832,689 A | 5/1989 | Mauerer et al. |
| 4,844,074 A | 7/1989 | Kurucz |
| 4,844,397 A | 7/1989 | Skakoon et al. |
| 4,847,470 A | 7/1989 | Bakke |
| 4,859,360 A | 8/1989 | Suzuki et al. |
| 4,874,033 A | 10/1989 | Chatelain et al. |
| 4,874,359 A | 10/1989 | White et al. |
| 4,878,537 A | 11/1989 | Verkaart |
| 4,878,588 A | 11/1989 | Ephraim |
| 4,883,117 A | 11/1989 | Dobbs et al. |
| 4,894,207 A | 1/1990 | Archer et al. |
| 4,900,308 A | 2/1990 | Verkaart |
| 4,904,848 A | 2/1990 | Colevas |
| 4,906,816 A | 3/1990 | van Leerdam |
| 4,910,386 A | 3/1990 | Johnson |
| 4,916,386 A | 4/1990 | Schulz |
| 4,923,681 A | 5/1990 | Cox et al. |
| 4,934,152 A | 6/1990 | Templeton |
| 4,934,336 A | 6/1990 | White |
| 4,935,604 A | 6/1990 | Allen et al. |
| 4,936,828 A | 6/1990 | Chiang |
| 4,961,320 A | 10/1990 | Gutmann |
| 4,991,976 A | 2/1991 | Byles |
| 4,994,021 A | 2/1991 | Smith et al. |
| 5,000,581 A | 3/1991 | Yata et al. |
| 5,013,889 A | 5/1991 | Bakke |
| 5,019,047 A | 5/1991 | Kriesel |
| 5,040,380 A | 8/1991 | Gregory |
| 5,042,455 A | 8/1991 | Yue et al. |
| 5,059,182 A | 10/1991 | Laing |
| 5,061,241 A | 10/1991 | Stephens, Jr. et al. |
| 5,061,630 A | 10/1991 | Knopf et al. |
| 5,063,994 A | 11/1991 | Verkaart |
| 5,073,167 A | 12/1991 | Carr et al. |
| 5,074,658 A | 12/1991 | Talvarides et al. |
| 5,075,167 A | 12/1991 | Yamauchi et al. |
| 5,081,697 A | 1/1992 | Manella |
| 5,096,078 A | 3/1992 | McQueeny |
| 5,096,822 A | 3/1992 | Rosenkrans, Jr. et al. |
| 5,097,898 A | 3/1992 | Verkaart |
| 5,103,817 A | 4/1992 | Reisdorf et al. |
| 5,106,373 A | 4/1992 | Augustine et al. |
| 5,108,372 A | 4/1992 | Swenson |
| 5,125,069 A | 6/1992 | O'Boyle |
| 5,125,900 A | 6/1992 | Teves |
| 5,129,033 A | 7/1992 | Ferrara et al. |
| 5,153,827 A | 10/1992 | Coutre et al. |
| 5,169,389 A | 12/1992 | Kriesel |
| 5,180,896 A | 1/1993 | Gibby et al. |
| 5,183,994 A | 2/1993 | Bowles, Sr. et al. |
| 5,184,613 A | 2/1993 | Mintz |
| 5,186,057 A | 2/1993 | Everhart |
| 5,195,976 A | 3/1993 | Swenson |
| 5,205,820 A | 4/1993 | Kriesel |
| 5,211,631 A | 5/1993 | Sheaff |
| 5,217,064 A | 6/1993 | Kellow et al. |
| 5,232,439 A | 8/1993 | Campbell et al. |
| 5,241,951 A | 9/1993 | Mason et al. |
| 5,243,172 A | 9/1993 | Hazan et al. |
| 5,243,833 A | 9/1993 | Coelho et al. |
| 5,245,693 A * | 9/1993 | Ford et al. .................. 392/470 |
| 5,250,032 A | 10/1993 | Carter, Jr. et al. |
| 5,254,094 A | 10/1993 | Starkey et al. |
| 5,261,411 A | 11/1993 | Hughes |
| 5,261,875 A | 11/1993 | Spears et al. |
| 5,263,323 A | 11/1993 | Maus et al. |
| 5,263,929 A | 11/1993 | Falcone et al. |
| 5,269,749 A | 12/1993 | Koturov |
| 5,276,310 A | 1/1994 | Schmidt et al. |
| 5,279,558 A | 1/1994 | Kriesel |
| 5,279,598 A | 1/1994 | Sheaff |
| 5,282,264 A | 1/1994 | Reeves et al. |
| 5,282,683 A | 2/1994 | Brett |
| 5,290,222 A | 3/1994 | Feng et al. |
| 5,290,230 A | 3/1994 | Ainsworth et al. |
| 5,296,684 A | 3/1994 | Essig et al. |
| 5,297,234 A | 3/1994 | Harms et al. |
| 5,308,335 A | 5/1994 | Ross et al. |
| 5,315,830 A | 5/1994 | Doke et al. |
| 5,318,540 A | 6/1994 | Athayde et al. |
| 5,330,431 A | 7/1994 | Herskowitz |
| 5,333,326 A | 8/1994 | Faries, Jr. et al. |
| 5,338,157 A | 8/1994 | Blomquist |
| 5,342,313 A | 8/1994 | Campbell et al. |
| 5,345,923 A | 9/1994 | Luebke et al. |
| 5,348,539 A | 9/1994 | Herskowitz |
| 5,364,371 A | 11/1994 | Kamen |
| 5,364,385 A | 11/1994 | Harms et al. |
| 5,370,674 A | 12/1994 | Farrell |
| 5,381,510 A | 1/1995 | Ford et al. |
| 5,389,078 A | 2/1995 | Zalesky et al. |
| 5,392,025 A | 2/1995 | Figh et al. |
| 5,397,875 A | 3/1995 | Bechtold, Jr. |
| 5,399,007 A | 3/1995 | Marconet |
| 5,399,166 A | 3/1995 | Laing |
| 5,408,576 A | 4/1995 | Bishop |
| 5,408,577 A | 4/1995 | Weber, Jr. et al. |
| 5,411,480 A | 5/1995 | Kriesel |
| 5,411,482 A | 5/1995 | Campbell |
| 5,415,282 A | 5/1995 | Kienholz |
| 5,417,274 A | 5/1995 | Verkaart |
| 5,420,962 A | 5/1995 | Bakke |
| 5,423,759 A | 6/1995 | Campbell |
| 5,424,512 A | 6/1995 | Turetta et al. |
| 5,433,704 A | 7/1995 | Ross et al. |
| 5,451,209 A | 9/1995 | Ainsworth et al. |
| 5,474,538 A | 12/1995 | Stihler et al. |
| 5,482,373 A | 1/1996 | Hutchinson |
| 5,483,799 A | 1/1996 | Dalto |
| 5,485,408 A | 1/1996 | Blomquist |
| 5,492,534 A | 2/1996 | Athayde et al. |
| 5,494,196 A | 2/1996 | Tyner |
| 5,512,043 A | 4/1996 | Verkaart |
| 5,514,095 A | 5/1996 | Brightbill et al. |
| 5,523,055 A | 6/1996 | Hansen et al. |
| 5,531,697 A * | 7/1996 | Olsen .................. A61M 5/142 128/DIG. 12 |
| 5,531,698 A | 7/1996 | Olsen |
| 5,538,399 A | 7/1996 | Johnson |
| 5,540,561 A | 7/1996 | Johnson |
| 5,564,915 A | 10/1996 | Johnson |
| 5,567,119 A | 10/1996 | Johnson |
| 5,567,136 A | 10/1996 | Johnson |
| 5,572,873 A | 11/1996 | Lavigne et al. |
| 5,575,563 A | 11/1996 | Chiu et al. |
| 5,584,811 A | 12/1996 | Ross et al. |
| 5,590,648 A | 1/1997 | Mitchell et al. |
| 5,609,784 A | 3/1997 | Davenport |
| RE35,501 E | 5/1997 | Ross et al. |
| 5,634,426 A | 6/1997 | Tomlinson et al. |
| 5,647,854 A | 7/1997 | Olsen et al. |
| 5,649,910 A | 7/1997 | Kriesel et al. |
| 5,653,905 A | 8/1997 | McKinney |
| 5,658,250 A | 8/1997 | Blomquist et al. |
| 5,658,252 A | 8/1997 | Johnson |
| 5,658,478 A | 8/1997 | Roeschel et al. |

(56) References Cited

U.S. PATENT DOCUMENTS

| | | |
|---|---|---|
| 5,661,978 A | 9/1997 | Holmes et al. |
| 5,662,611 A | 9/1997 | Beiser et al. |
| 5,669,877 A | 9/1997 | Blomquist |
| 5,678,925 A | 10/1997 | Garmaise et al. |
| 5,681,284 A | 10/1997 | Herskowitz |
| 5,683,381 A | 11/1997 | Carr et al. |
| 5,690,614 A | 11/1997 | Carr et al. |
| 5,695,473 A | 12/1997 | Olsen |
| 5,707,151 A | 1/1998 | Parker et al. |
| 5,707,431 A | 1/1998 | Verkaart et al. |
| 5,713,864 A | 2/1998 | Verkaart |
| 5,720,728 A | 2/1998 | Ford |
| 5,729,653 A | 3/1998 | Magliochetti et al. |
| 5,733,263 A | 3/1998 | Wheatman |
| 5,738,442 A | 4/1998 | Paron et al. |
| 5,743,878 A | 4/1998 | Ross et al. |
| 5,744,806 A | 4/1998 | Frojd |
| 5,755,275 A | 5/1998 | Rose et al. |
| 5,772,409 A | 6/1998 | Johnson et al. |
| 5,779,364 A | 7/1998 | Cannnelongo et al. |
| 5,786,568 A | 7/1998 | Mckinney |
| 5,788,669 A | 8/1998 | Peterson |
| 5,788,671 A | 8/1998 | Johnson |
| 5,805,455 A | 9/1998 | Lipps |
| 5,806,528 A | 9/1998 | Magliochetti |
| 5,807,332 A | 9/1998 | Augustine et al. |
| 5,810,771 A | 9/1998 | Blomquist |
| 5,816,797 A | 10/1998 | Shoenfeld |
| 5,817,146 A | 10/1998 | Augustine |
| 5,823,746 A | 10/1998 | Johnson |
| 5,824,000 A | 10/1998 | Pavlo et al. |
| 5,829,880 A | 11/1998 | Diedrich |
| 5,840,068 A | 11/1998 | Cartledge |
| 5,858,303 A | 1/1999 | Schiffmann et al. |
| 5,862,672 A | 1/1999 | Faries, Jr. et al. |
| 5,875,282 A | 2/1999 | Jordan et al. |
| 5,876,370 A | 3/1999 | Blomquist |
| 5,879,143 A | 3/1999 | Cote et al. |
| 5,879,329 A | 3/1999 | Ginsburg |
| 5,891,096 A | 4/1999 | Hyun et al. |
| 5,893,843 A | 4/1999 | Rodrigues |
| 5,897,207 A | 4/1999 | Hartmann |
| 5,910,210 A | 6/1999 | Violi et al. |
| 5,919,218 A | 7/1999 | Carr |
| 5,924,289 A | 7/1999 | Bishop, II |
| 5,928,196 A | 7/1999 | Johnson et al. |
| 5,935,099 A | 8/1999 | Peterson et al. |
| 5,935,106 A | 8/1999 | Olsen |
| 5,954,485 A | 9/1999 | Johnson et al. |
| 5,954,700 A | 9/1999 | Kovelman |
| 5,961,492 A | 10/1999 | Kriesel et al. |
| 5,961,700 A | 10/1999 | Oliver |
| 5,961,866 A | 10/1999 | Hansen |
| 5,977,520 A | 11/1999 | Madson, Jr. et al. |
| 5,986,239 A | 11/1999 | Corrigan, III |
| 5,989,238 A | 11/1999 | Ginsburg |
| 5,997,927 A | 12/1999 | Gics |
| 6,024,539 A | 2/2000 | Blomquist |
| 6,035,102 A | 3/2000 | Bakke |
| 6,039,926 A | 3/2000 | Goldman |
| 6,045,648 A | 4/2000 | Palmgren et al. |
| 6,062,429 A | 5/2000 | West et al. |
| 6,096,007 A | 8/2000 | Haan et al. |
| 6,117,122 A | 9/2000 | Din et al. |
| 6,124,572 A | 9/2000 | Spilgner et al. |
| 6,129,702 A | 10/2000 | Woias et al. |
| 6,139,528 A | 10/2000 | Kistner et al. |
| 6,142,974 A | 11/2000 | Kristher et al. |
| 6,146,359 A | 11/2000 | Carr et al. |
| 6,158,458 A | 12/2000 | Ryan |
| 6,164,469 A | 12/2000 | Sartore |
| 6,174,300 B1 | 1/2001 | Kriesel et al. |
| 6,175,099 B1 | 1/2001 | Shei et al. |
| 6,175,688 B1 | 1/2001 | Cassidy et al. |
| 6,221,045 B1 | 4/2001 | Duchon et al. |
| 6,221,051 B1 | 4/2001 | Hjertman et al. |
| 6,236,809 B1 | 5/2001 | Cassidy et al. |
| 6,248,077 B1 | 6/2001 | Elson et al. |
| 6,254,572 B1 | 7/2001 | Knipfer et al. |
| 6,257,759 B1 | 7/2001 | Witonsky et al. |
| 6,259,067 B1 | 7/2001 | Faries, Jr. et al. |
| 6,261,261 B1 * | 7/2001 | Gordon ............... A61M 5/44 604/113 |
| 6,264,049 B1 | 7/2001 | Shteynberg |
| 6,294,762 B1 | 9/2001 | Faries, Jr. et al. |
| 6,316,750 B1 | 11/2001 | Levin |
| 6,334,707 B1 | 1/2002 | Ku |
| 6,371,121 B1 | 4/2002 | Faries, Jr. et al. |
| 6,376,805 B2 | 4/2002 | Faries, Jr. et al. |
| 6,384,380 B1 | 5/2002 | Faries, Jr. et al. |
| 6,464,666 B1 | 10/2002 | Augustine et al. |
| 6,467,953 B1 | 10/2002 | Faries, Jr. et al. |
| 6,480,257 B2 | 11/2002 | Cassidy et al. |
| 6,524,239 B1 | 2/2003 | Reed et al. |
| 6,553,336 B1 | 4/2003 | Johnson et al. |
| 6,566,631 B1 | 5/2003 | Faries, Jr. et al. |
| 6,607,027 B2 | 8/2003 | Bosch et al. |
| 6,641,556 B1 | 11/2003 | Shigezawa |
| 6,641,602 B2 | 11/2003 | Balding |
| 6,649,040 B1 | 11/2003 | Mirchi et al. |
| 6,660,974 B2 | 12/2003 | Faries, Jr. et al. |
| 6,722,782 B2 | 4/2004 | Faries, Jr. et al. |
| 6,736,788 B1 | 5/2004 | Mongomery et al. |
| 6,740,059 B2 | 5/2004 | Flaherty |
| 6,748,164 B1 | 6/2004 | Kuzyk |
| 6,768,085 B2 | 7/2004 | Faries, Jr. et al. |
| 6,788,885 B2 | 9/2004 | Mitsunaga et al. |
| 6,788,997 B1 | 9/2004 | Frederick |
| 6,824,528 B1 | 11/2004 | Faries, Jr. et al. |
| 6,850,252 B1 | 2/2005 | Hoffberg |
| 6,860,271 B2 | 3/2005 | Faries, Jr. et al. |
| 6,869,538 B2 | 3/2005 | Yu et al. |
| 6,967,575 B1 | 11/2005 | Dohrmann et al. |
| 7,031,602 B2 | 4/2006 | Faries, Jr. et al. |
| 7,031,778 B2 | 4/2006 | Hsiung et al. |
| 7,041,941 B2 | 5/2006 | Faries, Jr. et al. |
| 7,090,658 B2 | 8/2006 | Faries, Jr. et al. |
| 7,176,030 B2 | 2/2007 | Faries, Jr. et al. |
| 7,238,171 B2 | 7/2007 | Faries, Jr. et al. |
| 7,262,698 B1 | 8/2007 | Frederick et al. |
| 7,276,675 B2 | 10/2007 | Faries, Jr. et al. |
| 7,307,245 B2 | 12/2007 | Faries, Jr. et al. |
| 7,326,882 B2 | 2/2008 | Faries, Jr. et al. |
| 7,417,205 B2 | 8/2008 | Faries, Jr. et al. |
| 7,540,864 B2 | 6/2009 | Faries, Jr. et al. |
| 7,608,460 B2 | 10/2009 | Reed et al. |
| 7,611,504 B1 | 11/2009 | Faries, Jr. et al. |
| 7,726,876 B2 | 6/2010 | Laverdiere et al. |
| 7,740,611 B2 | 6/2010 | Faries, Jr. et al. |
| 7,942,851 B2 | 5/2011 | Faries, Jr. et al. |
| 8,226,293 B2 | 7/2012 | Faries, Jr. et al. |
| 8,226,605 B2 | 7/2012 | Faries, Jr. et al. |
| 8,313,462 B2 | 11/2012 | Faries, Jr. et al. |
| 8,444,599 B2 | 5/2013 | Faries, Jr. et al. |
| 8,487,738 B2 | 7/2013 | Faries, Jr. et al. |
| 8,636,691 B2 | 1/2014 | Faries, Jr. et al. |
| 8,734,404 B2 | 5/2014 | Faries, Jr. |
| 8,734,405 B2 | 5/2014 | Faries, Jr. |
| 8,821,011 B2 | 9/2014 | Faries, Jr. et al. |
| 8,845,586 B2 | 9/2014 | Faries, Jr. et al. |
| 8,920,372 B2 | 12/2014 | Faries, Jr. et al. |
| 8,920,387 B2 | 12/2014 | Faries, Jr. et al. |
| 9,211,381 B2 | 12/2015 | Faries, Jr. et al. |
| 2001/0009610 A1 * | 7/2001 | Augustine et al. ............ 392/470 |
| 2002/0041621 A1 | 4/2002 | Faries et al. |
| 2002/0081109 A1 | 6/2002 | Mitsunaga et al. |
| 2002/0147426 A1 | 10/2002 | Faries, Jr. et al. |
| 2002/0151854 A1 | 10/2002 | Duchon et al. |
| 2002/0156451 A1 | 10/2002 | Lenker |
| 2002/0158058 A1 | 10/2002 | Faries, Jr. et al. |
| 2002/0158085 A1 | 10/2002 | Faries, Jr. et al. |
| 2002/0184906 A1 | 12/2002 | Faries, Jr. et al. |
| 2003/0000939 A1 | 1/2003 | Faries, Jr. et al. |
| 2003/0004470 A1 | 1/2003 | Hickerson et al. |

(56) References Cited

U.S. PATENT DOCUMENTS

| | | |
|---|---|---|
| 2003/0114795 A1 | 6/2003 | Faries, Jr. et al. |
| 2003/0135388 A1 | 7/2003 | Martucci et al. |
| 2003/0216831 A1 | 11/2003 | Hart et al. |
| 2003/0218003 A1 | 11/2003 | Ellis et al. |
| 2003/0222933 A1 | 12/2003 | Choi |
| 2004/0170409 A1 | 9/2004 | Faries, Jr. et al. |
| 2004/0189258 A1 | 9/2004 | Lehmann et al. |
| 2004/0247016 A1 | 12/2004 | Faries, Jr. et al. |
| 2005/0059952 A1 | 3/2005 | Giuliano et al. |
| 2005/0070845 A1 | 3/2005 | Faries, Jr. et al. |
| 2005/0142013 A1 | 6/2005 | Faries, Jr. et al. |
| 2005/0222933 A1 | 10/2005 | Wesby |
| 2005/0241026 A1 | 10/2005 | Esler et al. |
| 2005/0242930 A1 | 11/2005 | Nicolson et al. |
| 2006/0020255 A1 | 1/2006 | Cassidy et al. |
| 2006/0100578 A1 | 5/2006 | Lieberman |
| 2006/0253075 A1 | 11/2006 | Faries, Jr. et al. |
| 2006/0291533 A1 | 12/2006 | Faries, Jr. et al. |
| 2007/0000910 A1 | 1/2007 | Faries, Jr. et al. |
| 2007/0015975 A1 | 1/2007 | Faries, Jr. et al. |
| 2007/0106243 A1 | 5/2007 | Faries, Jr. et al. |
| 2007/0142773 A1 | 6/2007 | Rosiello et al. |
| 2007/0161952 A1 | 7/2007 | Faries, Jr. et al. |
| 2007/0197878 A1 | 8/2007 | Shklarski |
| 2007/0215018 A1 | 9/2007 | Faries, Jr. et al. |
| 2008/0021392 A1 | 1/2008 | Lurvey et al. |
| 2008/0058697 A1 | 3/2008 | Kamen et al. |
| 2008/0147016 A1 | 6/2008 | Faries, Jr. et al. |
| 2008/0205481 A1 | 8/2008 | Faries et al. |
| 2010/0059498 A1 | 3/2010 | Hansen et al. |
| 2010/0082459 A1 | 4/2010 | Tusa et al. |
| 2010/0111135 A1 | 5/2010 | Faries, Jr. et al. |
| 2010/0168671 A1 | 7/2010 | Faries, Jr. et al. |
| 2010/0222762 A1 | 9/2010 | Faries, Jr. et al. |
| 2010/0222763 A1 | 9/2010 | Faries, Jr. et al. |
| 2011/0297831 A1 | 12/2011 | Yao et al. |
| 2011/0307274 A1 | 12/2011 | Thompson et al. |
| 2012/0191050 A1 | 7/2012 | Faries, Jr. |
| 2012/0265336 A1 | 10/2012 | Mallett et al. |
| 2012/0285236 A1 | 11/2012 | Haartsen et al. |
| 2013/0197437 A1 | 8/2013 | Faries et al. |
| 2013/0253952 A1 | 9/2013 | Burke et al. |
| 2014/0231406 A1 | 8/2014 | Tsang et al. |
| 2014/0236615 A1 | 8/2014 | Ragusky et al. |
| 2016/0074599 A1 | 3/2016 | Faries, Jr. et al. |

FOREIGN PATENT DOCUMENTS

| | | |
|---|---|---|
| DE | 19752578 A1 | 6/1999 |
| EP | 0927552 A1 | 7/1999 |
| FR | 2786057 | 5/2000 |
| GB | 2029677 A | 3/1980 |
| GB | 2274514 A | 7/1994 |
| JP | 58-030666 | 2/1983 |
| JP | 2000-300666 | 10/2000 |
| NZ | 331678 A | 3/2000 |
| WO | 9221272 | 12/1992 |
| WO | 9838953 | 9/1998 |
| WO | 98/45658 A1 | 10/1998 |
| WO | 9845658 | 10/1998 |
| WO | 99/22786 A1 | 5/1999 |
| WO | 9926690 | 6/1999 |
| WO | 9922786 | 9/1999 |
| WO | 9958177 | 11/1999 |

OTHER PUBLICATIONS

Minco Products, Inc., Bulletin CTI98, 1996.
Eurotherm Controls, Inc. Model 2116 Temperature Controller, 1997.
Ellenwood, Drop Detector, IBM Technical Bulletin, vol. 12, No. 5, Oct. 1969.
CBI Medical, Inc. IV Fluid Warmer Model 8362, 1992.
Cahill, New Name, New Helmsman, JEMS, Aug. 1996, 3 pages.
Cbi Healthcare Systems, Inc. Controlled Temperature Cabinet Syste, JEMS, Mar. 17, 1997, 1 page.
Koolatron, P-34 PC-3 Precision Control Themolectric Cooler/Warmer, Jan. 1998, 1 page.
Koolatron, Canadian Company announces the release of a precision control unit, Aug. 1997, 1 page.
Anton, 500 miles from nowhere, it'll give you a cold drink or a warm burger . . . , Technology Update, 1993, 1 page.
Koolatron, 1997 U.S. $Price List, 1997, 4 pages.
Kellow et al, Drug Adulteration in Prehospital Emergency Medical Services, Oct. 1994, 43 pages.
PCT International Search Report and Written Opinion, PCT/US2014/015944, Jun. 2, 2014, 11 pages.
PCT International Search Report and Written Opinion, PCT/US201/016869, Jun. 27, 2014, 10 pages.

\* cited by examiner

METHOD AND APPARATUS FOR HEATING SOLUTIONS WITHIN INTRAVENOUS LINES TO DESIRED TEMPERATURES DURING INFUSION

CROSS-REFERENCE TO RELATED APPLICATIONS

This application is a continuation of U.S. patent application Ser. No. 10/016,128, entitled "Method and Apparatus for Heating Solutions Within Intravenous Lines to Desired Temperatures During Infusion" and filed Dec. 17, 2001, now U.S. Pat. No. 8,226,605, the disclosure of which is incorporated herein by reference in its entirety.

BACKGROUND OF THE INVENTION

1. Technical Field

The present invention pertains to devices for warming intravenous (IV) solution during infusion into a patient. In particular, the present invention pertains to a device for receiving and heating a preformed IV tubing cassette or cartridge connected to an IV line to warm solution flowing within the line to a desired temperature during infusion into a patient.

2. Discussion of Related Art

Intravenous (IV) fluids are typically infused into a patient utilizing a liquid filled bag or container and an IV fluid line. The fluids are generally delivered from the container to the patient via gravitational forces and/or applied pressure. It is important in many situations that the temperature of the fluid within the IV line be maintained within a desirable and safe temperature range upon entering the patient body so as to eliminate any potential for thermal shock and injury to the patient.

Accordingly, the related art provides several devices for controlling the temperature of fluid in an IV line for infusion into a patient. For example, U.S. Pat. No. 4,167,663 (Granzow, Jr. et al.) discloses a blood warming device including a housing with a heating compartment and an access door. The heating compartment includes a warming bag that is internally baffled to define a tortuous flow path and has an inlet port and an outlet port for allowing fluid to flow through the bag. The bag is sandwiched between a plate on the access door and an opposing plate within the heating compartment. The two plates include heating elements to heat the bag and the fluid flowing therein. The device further includes temperature sensors to measure the temperature of fluid flowing within the bag and control circuitry to control the heating elements in accordance with the measured temperatures.

U.S. Pat. No. 4,356,383 (Dahlberg et al.) discloses a fluid heating apparatus including a box-shaped member having an enclosure member or cap, a conduit or bag disposed between the box-shaped member and cap and a pair of heating plates respectively connected to the box-shaped member and cap to abut opposing sides of the conduit and heat fluid flowing therethrough. A temperature sensing device is positioned for engaging the conduit at a predetermined location to sense the temperature of fluid within the conduit. The apparatus further includes a contact member to engage the conduit at a predetermined location for compressing the conduit to constrict the cross-sectional area of the flow passage when the flow rate of fluid is below a predetermined flow rate.

U.S. Pat. No. 5,245,693 (Ford et al.) discloses an apparatus for heating parenteral fluids for intravenous delivery to a patient. The apparatus includes a disposable cassette which is made up of a unitary member divided to form a serpentine flow path by a plurality of path separators. Thin, flexible metallic foil membranes are sealingly joined to the unitary member on the upper and bottom surfaces thereof to form an enclosed, fluid-tight serpentine flow path between the plurality of path separators. The entire periphery of the unitary member and heat conductive foil membranes are sealingly held by a framework. The disposable cassette slides between first and second heating blocks which contact the heat conductive foil membranes so as to provide heat transfer to fluid flowing in the serpentine flow path. The heating blocks are designed to provide a gradation of heat energy where more heat is energy is available for transfer to the fluid at the inlet end of the serpentine flow path than that available for transfer to the fluid at the serpentine flow path outlet end.

U.S. Pat. No. 5,381,510 (Ford et al.) discloses a disposable, in-line heating cassette and apparatus for raising the temperature of fluids. The cassette comprises a spacer defining a sinuous or serpentine flow pathway interposed between flexible foils and mounted on a frame. The frame comprises inlet and outlet tubes and related input and output parts which communicate with the serpentine path. Juxtaposed heating plates in direct contact with the cassette substantially contact the entire heating surface of the foils, thereby providing a thermal path from the heating plate to the foil and further to the fluid. The heating plates have several electrically conductive strips thereon for generating a gradation of heat energy where more heat energy is available for transfer at the inlet end than at the outlet end of the serpentine flow path.

U.S. Pat. No. 6,175,688 (Cassidy et al.) discloses an intravenous fluid heater dimensioned to be wearable adjacent a patient intravenous fluid infusion situs. The heater includes a heat exchanger for defining a flow path through the heater for fluid to be infused via the infusion situs. At least one controllable heating element is provided for heating the fluid in the flow path by heat conduction thereto through the heat exchanger. Sensors are included for sensing respective temperatures of entering and exiting fluids of the flow path. A controller controls heating of the fluid in the flow path based on temperatures of the exiting fluids to cause the fluid in the flow path to be substantially uniformly heated to a desired infusion temperature prior to exiting the heater.

U.S. Pat. No. 6,261,261 (Gordon) discloses an infrared heating device for prewarming solutions that includes a cassette having a predetermined length of tubing connectable between an IV solution source and an infusion site for a patient. An infrared energy-generating sheet is positioned onto the cassette adjacent the IV tubing. In one embodiment of the device, the IV tubing is arranged in a spiral path on the cassette.

The related art devices described above suffer from several disadvantages. In particular, the Granzow, Jr. et al., Dahlberg et al., Ford et al. and Cassidy et al. devices each generally employ housings that inhibit viewing of fluid during treatment. Thus, the fluid may incur certain undesirable conditions within the devices (e.g., contamination, air bubbles, etc.) that are beyond the view of, and may be undetected by, an operator, thereby risking serious injury to a patient. Further, these devices tend to employ heat exchangers generally with a serpentine fluid flow path defined therein that typically includes a plurality of overlapping fluid flow passageways. The path generally includes dimensions different than those of the fluid lines, thereby tending to affect the rate of fluid flow and, consequently, the amount of thermal energy required to heat the fluid to a desired temperature. As a result, the devices may need to further employ flow sensors to measure and account for changes in fluid flow in order to ensure maintenance of proper fluid temperature, thereby increasing system complexity and costs. Moreover, the overlapping passageways tend to confine thermal energy that may otherwise be distributed to heat the fluid, thereby limiting the device heating potential. The Gordon device utilizes a cassette with a fluid flow path formed of tubing. However, this device employs infrared radiation to thermally treat the fluid, thereby involving special safety measures and requiring additional components to isolate the radiation from the patient. In addition, the above-described systems of the related art include heat exchangers or fluid flow paths including inlets separated from fluid outlets, thereby tending to increase complexity of connections and installation for use with an infusion apparatus.

OBJECTS AND SUMMARY OF THE INVENTION

Accordingly, it is an object of the present invention to warm solution within an IV line during infusion by heating a preformed IV tubing cassette or cartridge connected to and receiving solution from the IV line.

It is another object of the present invention to uniformly heat an IV tubing cassette or cartridge containing solution from an IV line by simultaneously heating opposing cassette surfaces.

Yet another object of the present invention is to disable operation of an IV solution warming device in response to detecting the absence of a cassette within that device.

Still another object of the present invention is to configure an IV tubing cassette or cartridge to occupy a minimal amount of warming device housing space, while providing sufficient residence time for fluid to be heated to a desired temperature within the device.

A further object of the present invention is to thermally treat a warming device IV tubing cassette or cartridge containing fluid, while enabling viewing of the fluid within the device.

Yet another object of the present invention is to heat IV solution with a warming device employing an IV cassette or cartridge including tubing arranged to form concentric passages that alternately direct IV solution flow in opposing directions to enhance thermal transfer between the passages during solution warming.

The aforesaid objects may be achieved individually and/or in combination, and it is not intended that the present invention be construed as requiring two or more of the objects to be combined unless expressly required by the claims attached hereto.

According to the present invention, an IV line temperature controlled warming device includes a housing and a fluid cassette or cartridge that receives fluid from an IV line and includes intravenous line tubing arranged in a preformed configuration to enable the IV line fluid to flow therethrough. The preformed configuration includes tubing sections arranged in generally circular and concentric portions and a central serpentine tubing section that includes a generally 'S'-shaped configuration. The serpentine section basically reverses fluid flow and facilitates flow in opposing directions within adjacent tubing sections. The fluid cassette is retained within the device on a base plate partially disposed within a device housing interior, while a housing cover is selectively opened and closed to permit access to the base plate. The base plate includes a heater plate disposed thereon, while the cover and heater plate each include heating elements to apply heat to opposing surfaces of the tubing cassette. The heating elements are controlled by a controller in response to measured temperatures of the heater plate and fluid. In addition, the device includes various safeguards that ensure device operation during appropriate conditions (e.g., appropriate temperatures, proper placement of a compatible cassette within the device, etc.).

The above and still further objects, features and advantages of the present invention will become apparent upon consideration of the following detailed description of specific embodiments thereof, particularly when taken in conjunction with the accompanying drawings, wherein like reference numerals in the various figures are utilized to designate like components.

DETAILED DESCRIPTION OF THE PREFERRED EMBODIMENTS

Figure 1:
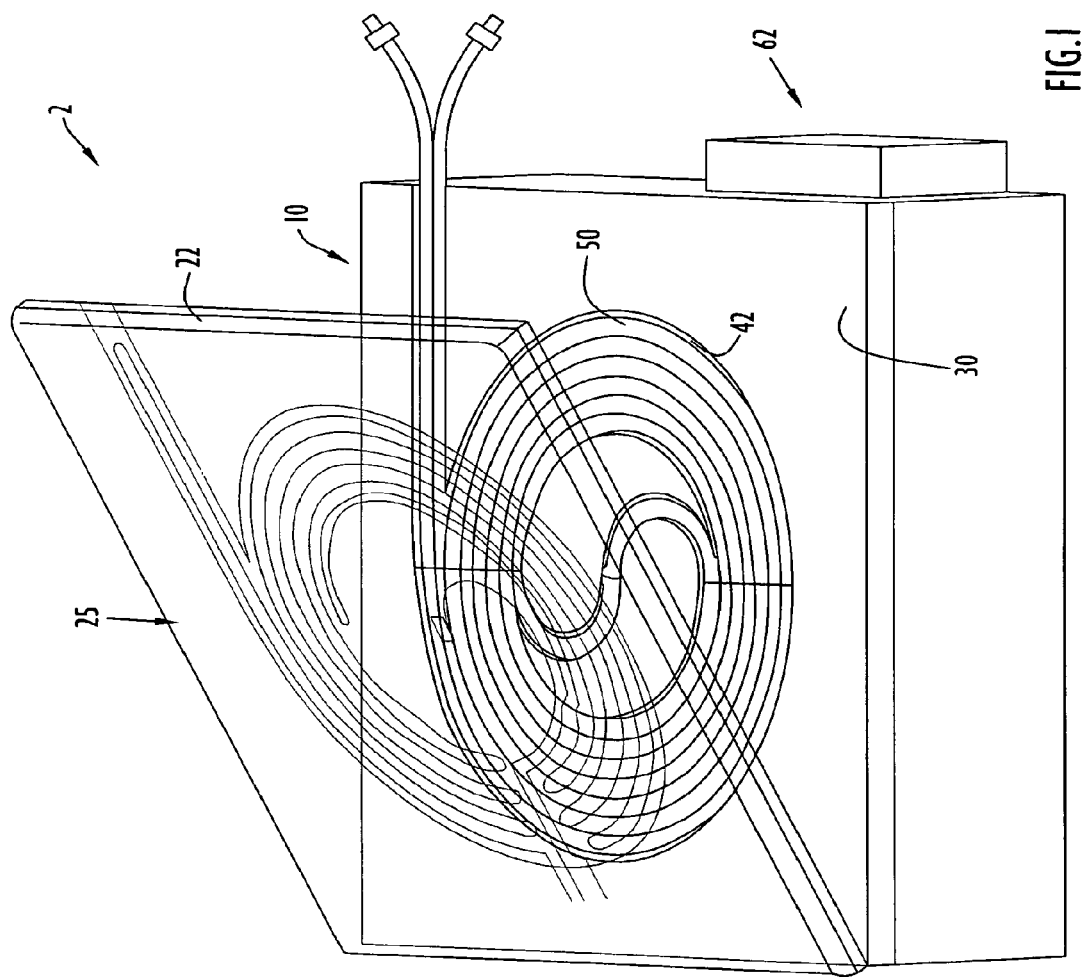
FIG. 1 is a view in perspective of an IV line temperature controlled warming device including an IV tubing cassette or cartridge disposed therein according to the present invention.

An IV line temperature controlled warming device for heating and maintaining fluids flowing within an IV fluid line at desired temperatures is illustrated in FIG. 1. Specifically, warming device 2 includes a housing 10 with a lid or cover 22 pivotally attached thereto. The warming device receives a tubing cassette or cartridge 50 that is typically connected to an intravenous line (IV) supplying intravenous solution from an IV solution bag or container to a patient. The device housing includes a base plate 30 to receive cassette 50 and a heater plate 42 disposed on the base plate beneath the cassette to heat a cassette bottom surface as described below. An additional heater or heating element 25 is disposed on cover 22 to heat the cassette top surface as described below. Thus, the cassette is disposed between the heater plate and cover heating elements to receive heat on opposing cassette surfaces for uniform heating of solution or other fluid flowing therein. A controller 62 is partially disposed within the housing to enable entry of desired solution temperatures and to control device operation as described below. The warming device may be oriented in a variety of positions (e.g., horizontally, vertically, etc.) and may be mounted to or supported by various structures (e.g., a patient arm or other body portion, swing arm, arm board, bed, bed rail, operating room or other table, IV pole, wall, floor, posts, etc.). The warming device is preferably positioned in close proximity to an infusion site of a patient in order to heat IV fluid (e.g., may heat fluid with or without skin contact), and may be portable for use in various locations. The warming device may be utilized for operating room, pre-op and/or post-op procedures or at any other times where infusion is being performed. In addition, a pre-heated IV solution bag or container may be used in conjunction with the warming device. In this case, the device is typically disposed at or near the patient infusion site and basically heats the fluid to compensate for heat loss during infusion due to exposure of the fluid to the ambient environment.

Figure 2:
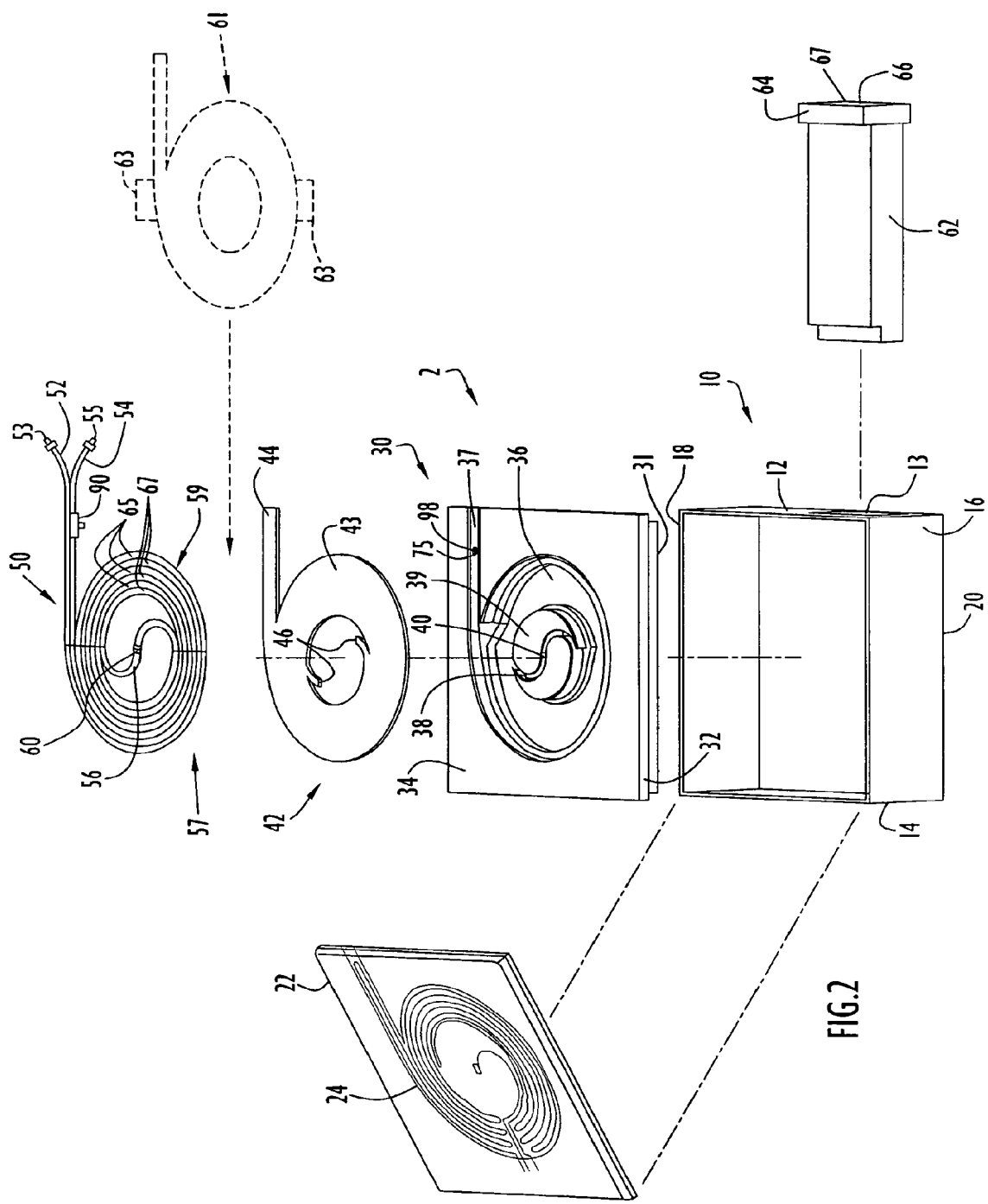
FIG. 2 is an exploded view in perspective of the warming device of FIG. 1.
Figure 3:
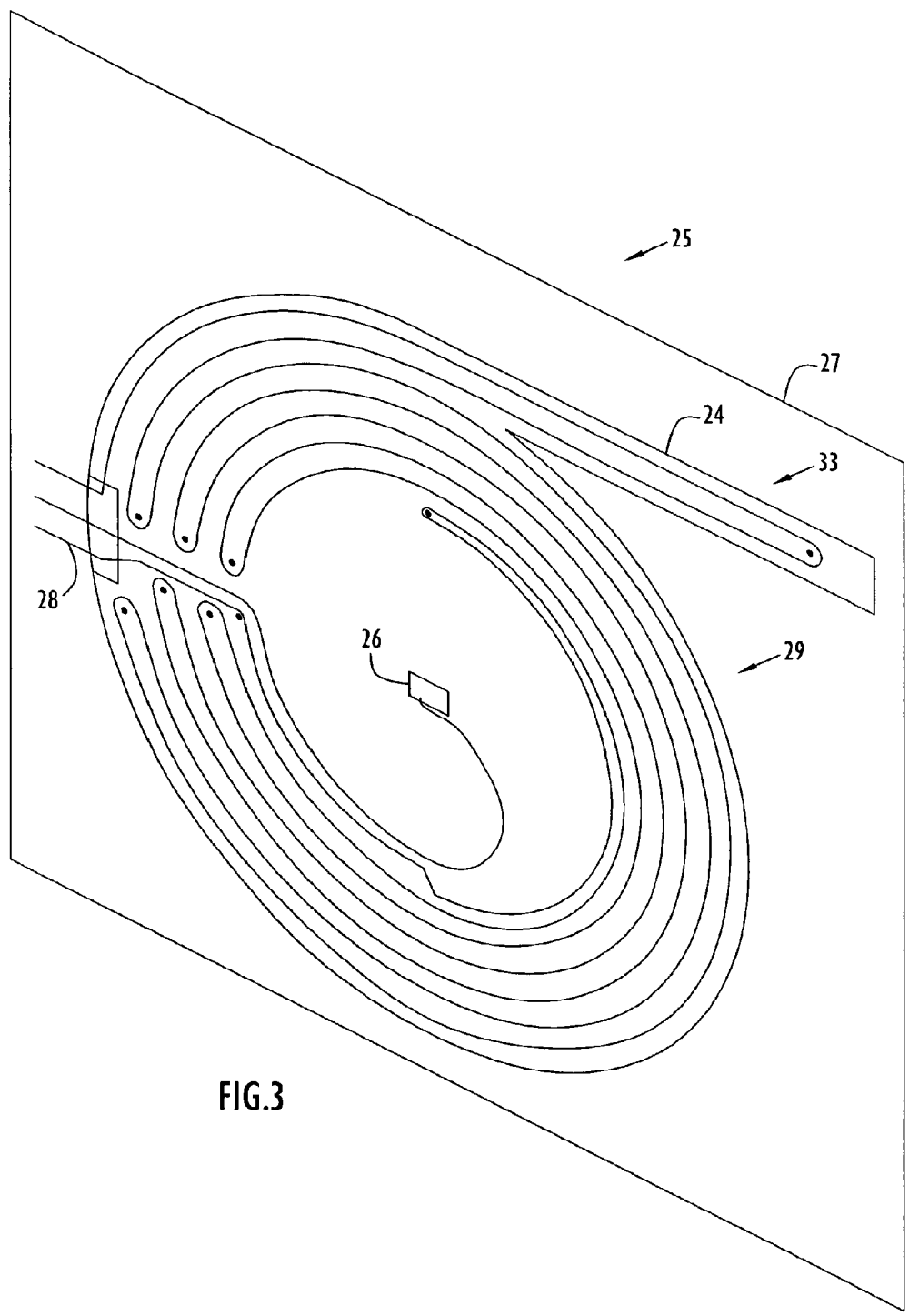
FIG. 3 is a view in perspective of a heating element for a cover of the warming device of FIG. 1.
Figure 4:
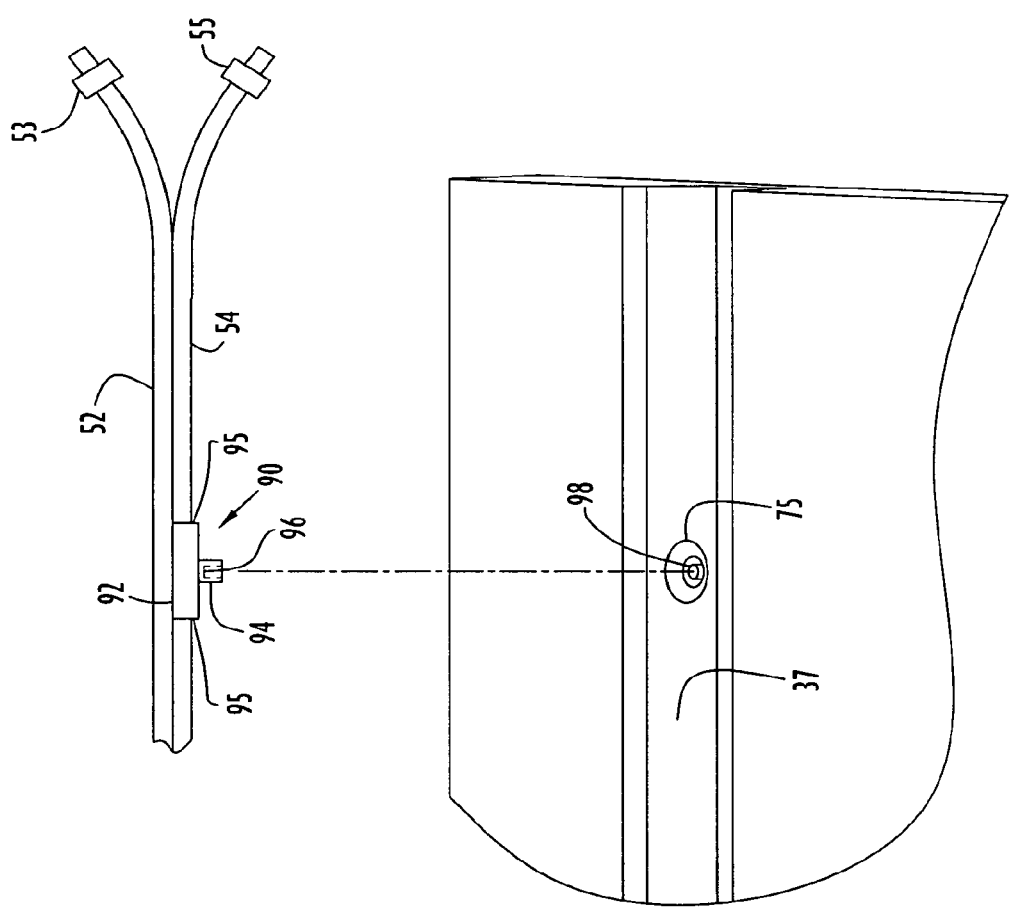
FIG. 4 is an exploded view in perspective of an outlet tubing portion of the cassette of FIG. 1 disposed on a device base plate and including a sensor fitting to measure temperature of fluid within the cassette.

Referring to FIGS. 2-4, housing 10 includes front and rear walls 12, 14, side walls 16, 18 and a bottom wall 20. Side walls 16, 18 are attached to and extend between front and rear walls 12, 14, while bottom wall 20 is attached to the bottom edges of the front, rear and side walls. The housing walls are substantially rectangular and collectively define a housing interior with an open top portion. It is to be understood that the terms "top", "bottom", "side", "front", "rear", "horizontal", "vertical", "upper", "lower", "up", "down", "height", "length", "width", "depth" and the like are used herein merely to describe points of reference and do not limit the present invention to any specific orientation or configuration. Front wall 12 includes a substantially rectangular opening 13 defined therein for receiving controller 62. The controller is disposed through the front wall and partially within the housing interior. The housing may be constructed of any suitable rigid material (e.g., plastic), and is preferably constructed of a substantially transparent material to permit viewing of the fluid within the cassette, especially during heating. This enables an operator to detect various conditions (e.g., contamination, air bubbles, etc.) that may cause injury to a patient. The housing basically houses the device electrical components and supports the base plate as described below.

Base plate 30 has a generally rectangular configuration and includes a lower portion 31 that is suitably dimensioned to fit within the housing open top portion. The base plate is constructed of a suitably rigid material (e.g., an acrylic resin) to receive and retain the heater plate and tubing cassette thereon as described below. The base plate is preferably transparent to enable viewing of intravenous fluid flowing within the cassette as described above. An upper portion 32 of the base plate has dimensions greater than those of lower portion 31 to permit the base plate to rest on the upper edges of the housing front, rear and side walls with the base plate lower portion slightly extending within the housing interior. An upper surface 34 of the base plate includes a generally annular recess or groove 36 defined therein. The groove basically forms a substantially circular engagement section 39 on the base plate upper surface within an area defined by a groove inner diameter or dimension. A channel 37 extends tangentially from a circumferential edge of the annular groove to a base plate front edge. Channel 37 includes an opening 75 for receiving a device temperature probe and a cassette temperature sensing fitting to measure temperature of fluid within the cassette as described below. A serpentine channel 38 including a generally 'S'-shaped configuration is defined within section 39 and facilitates proper alignment of cassette 50 within the device for temperature heating and measurement of fluid as described below. The ends of channel 38 emerge from section 39 to communicate with annular groove 36. A post 40 is disposed at the approximate center of channel 38 and is typically constructed of an electrically conductive material (e.g., copper). The post facilitates formation of a conductive path to enable device operation as described below.

Heater plate 42 includes a configuration compatible with the upper surface of base plate 30. Specifically, heater plate 42 includes a generally annular portion 43 with an elongated and generally rectangular projection 44 extending tangentially from an annular portion circumferential edge. The heater plate is preferably flat, but may include a grooved surface to receive cassette tubing sections or to form fluid flow paths to enable use of the device without the cassette. Channel projections 46 extend from the inner edge of the annular portion and are angularly spaced by approximately one-hundred eighty degrees. The channel projections are suitably configured and dimensioned to occupy initial portions of channel 38 of base plate 30 while permitting conductive post 40 to be exposed. Heater plate 42 includes a conventional or other heating element 80 (FIG. 5) disposed on the underside of the heater plate. The heating element is preferably in form of a conventional etched silicon rubber heating pad or other heater affixed to the heater plate underside by a pressure sensitive adhesive. Alternatively, the heating element may be contoured to a heater plate grooved surface or be attached to the flat surface via any conventional fastening techniques (e.g., adhesives, etc.). The heating element heats the heater plate and is coupled to a warming device control circuit to control heating of the cassette as described below. Heater plate annular portion 43 and projections 44, 46 are disposed within groove 36 and channels 37, 38 of the base plate, respectively, to enable the heater plate to heat an engaging surface of a tubing cassette placed thereon. The heater plate may be constructed of any thermally conductive materials.

Cassette 50 includes a configuration compatible with the base plate to facilitate placement of the cassette within the warming device. Specifically, the cassette includes an inlet portion 52, an outlet portion 54 adjacent the inlet portion and a cassette body 57 defining a fluid flow path. The cassette body includes tubing sections 59, preferably transparent, arranged in generally circular and concentric sections 65, 67. A central serpentine tubing section 56 includes a generally 'S'-shaped configuration that basically reverses fluid flow and facilitates flow in opposing directions within adjacent concentric tubing sections 65, 67. In other words, fluid enters the cassette via inlet portion 52 and flows through concentric sections 65 toward central serpentine tubing section 56. The serpentine section receives fluid from an innermost tubing section 65 and directs the fluid to flow in concentric sections 67 toward outlet portion 54. Thus, fluid flows in concentric sections 65 in a direction opposite to that of fluid flow in adjacent sections 67. The concentric tubing sections are in close proximity to each other to enable thermal transfer between adjacent sections. The cassette may include any quantity of tubing sections to produce a residence time within the warming device sufficient to heat the fluid. The concentric tubing sections may be spaced a slight distance from each other or be positioned to contact adjacent sections, while the tubing may be manipulated to form and maintain a cassette configuration via any conventional techniques or manufacturing processes (e.g., molded, glued, etc.). The serpentine tubing section facilitates alternate or opposing fluid flow directions (e.g., without utilizing overlapping or serpentine type configurations) and proper alignment of the cassette within the base plate as described below. However, the cassette may include any configuration reversing fluid flow direction, and may include overlapping or non-overlapping tubing sections. The cassette inlet, outlet and body may be constructed of a flexible plastic (e.g., polyvinyl chloride (PVC)) or any other material suitable for IV fluid line applications.

Inlet and outlet tubing portions 52, 54 are adjacent each other and extend tangentially from a circumferential edge of body 57. These tubing portions further include dimensions suitable for being received and retained within base plate channel 37. The inlet and outlet tubing portions terminate at respective inlet and outlet terminals 53, 55 that extend externally of the device housing when the cassette is received and retained within the base plate annular groove and channels. The inlet and outlet terminals include suitable connectors (e.g., Luer locks) to connect inlet and outlet tubing portions 52, 54 to any selected portions of an IV line. Serpentine tubing section 56 has dimensions sufficient to be retained within base plate channel 38 and basically facilitates appropriate alignment of the cassette within the base plate for heating and temperature measurement of the fluid. A contact 60 is disposed around and encircles a substantially central portion of serpentine tubing section 56. The contact is preferably constructed of an electrically conductive material (e.g., copper), and may be in any desired form (e.g., a metallic band, wrap, rod, fluid, etc.). The base plate configuration enables cassette contact 60 to contact conductive post 40 and a contact 26 of cover heating element 25 when the tubing cassette is placed within the base plate groove and channels and the cover is in a closed state. The post and contacts basically serve to form or complete an electrical path or circuit to enable device operation in response to proper placement of a compatible cassette within the device. The warming device may alternatively employ contacts or conductive members disposed on any device components at any locations to form an electrical path through a pressure switch that senses closure of the device on the cassette for proper operation. The pressure switch may further include a dual element sensor to measure fluid temperatures within the cassette inlet and outlet portions.

A sheet or backing 61 may be attached to the cassette top and/or bottom surface to secure the tubing arrangement thereon. The sheet may include an annular configuration similar to that of cassette 50, and may include engagement members or tabs 63 disposed on the sheet at any desired locations to facilitate manipulation of the cassette relative to the warming device (e.g., facilitate insertion and removal of the cassette within the warming device). The warming device may accommodate any quantity of cassettes, while the cassette may include any quantity of preformed tubing to form a plural level or layer cassette. In other words, the cassette may include any quantity of tubing sections disposed on any quantity of planes (e.g., stacked one above the other, etc.). This tends to provide additional residence or heating time for fluid within the cassette. The fluid flow path through the cassette may be formed in any manner, and may be defined by any structures (e.g., tubing, sealed channels, pools, chambers, etc.).

Flow of IV fluid through cassette 50 is described. Basically, fluid from an IV line enters the cassette at inlet terminal 53 and is directed in a winding pattern through concentric tubing sections 65 toward serpentine section 56. Upon reaching tubing section 56, the fluid is directed in an opposing direction through concentric tubing sections 67 toward outlet portion 54 to exit the cassette at outlet terminal 55 and return to the IV line or be directed to a desired location (e.g., an infusion site). In essence, fluid flowing within the cassette travels in opposing directions within adjacent concentric tubing sections of the cassette body. The flow pattern defined by the tubing cassette provides a greater residence time for fluid within the cassette, thereby extending the exposure of the fluid to heating elements within the device housing. Further, the flow pattern enhances heat exchange between adjacent tubing sections 65, 67 that contain fluid exposed to the heating elements for different intervals (e.g., fluid flowing within sections 67 toward outlet portion 54 has a greater residence time than fluid flowing in adjacent tubing sections 65 toward serpentine section 56). It is to be understood that the designation of portion 52 as the inlet portion and portion 54 as the outlet portion is for illustrative purposes only, since either portion may serve as an inlet or outlet portion depending upon the manner in which the terminals of the tubing cassette are connected to an IV line.

Cover or lid 22 is generally rectangular and pivotally connected to an upper edge of rear wall 14 to selectively control access to the housing. The cover includes an open bottom portion and is configured to receive and cover upper portion 32 of base plate 30. The cover may be connected in any suitable manner to the housing rear wall via any fastening devices (e.g., hinges, brackets, etc.), and may include a handle (not shown) or any other suitable device or structure to facilitate pivoting of the cover with respect to the housing. The cover may alternatively be connected to any of the housing walls or base plate, and may be constructed of any suitable materials (e.g., an acrylic resin). However, the cover is preferably constructed of a transparent material to enable viewing of intravenous fluid flowing within the tubing cassette as described above. A latching or locking mechanism (not shown) may be disposed on the cover and/or housing to secure the cover in a closed state and press the cover against the cassette to enhance contact between the cassette top and bottom surfaces and the cover heating element and heater plate, respectively.

The cover includes heating element 25 (FIG. 3) to apply heat to the cassette top surface. Specifically, heating element 25 is disposed on a cover interior surface in facing relation with the heater plate. The heating element is preferably implemented by a clear or transparent acrylic heater including a sheet 27 with electrically conductive wiring 24 embedded therein. The transparent heating element enables viewing of the fluid flowing within the cassette as described above. Wiring 24 is arranged within sheet 27 and, hence, on the cover to coincide with the tubing cassette received on the base plate. The configuration of the electrical wiring basically includes a generally annular body portion 29 with a tangentially extending section 33. These sections basically outline and are disposed coincident the corresponding body and inlet and outlet portions of the cassette to apply heat to those cassette sections. Contact 26 (e.g., an electrically conductive plate) is disposed on sheet 27 within the confines of wiring body portion 29 and facilitates formation of an electrical path from the cover heating element contact through cassette contact 60 to the base plate conductive post to enable device operation as described below. Wiring 24 further includes connection terminals 28 disposed toward a circumferential edge of wiring body portion 29 to connect the heating element to a device control circuit as described below.

In order to measure temperature of fluid within cassette 50, a fitting 90 is disposed within outlet portion 54 at a location toward outlet terminal 55. Fitting 90 (FIG. 4) includes a substantially cylindrical base portion 92 and a generally cylindrical projection 94 extending transversely relative to the cassette tubing from an intermediate section of the base portion. The base portion includes open ends 95 and a longitudinal channel defined therethrough to permit fluid flow through the base portion. The open ends are securable to outlet portion 54. Projection similarly includes open ends and facilitates access to the base portion channel. Fitting 90 typically includes a T-type configuration, however, any configuration (e.g., a Y-type fitting, cross fitting, coupling, etc.) may be utilized. Each base portion open end 95 may be secured to the outlet portion via any suitable connector, while the fitting is typically disposable with the cassette after each use to maintain fluid sterility. The fitting may be constructed of plastic or any other rigid material suitable for use with IV lines. A thermally conductive receptacle 96 is secured within projection 94 and extends partially within base portion 92 for contacting fluid flowing within the base portion channel. Receptacle 96 may be constructed of stainless steel or any other material having suitable thermal conductivity, and may be secured within the projection via any suitable securing techniques (e.g., friction fit, adhesives, etc.). The receptacle includes a generally cylindrical body with a closed distal end that extends partially within the base portion and an open proximal end for receiving a temperature probe or sensor 98 as described below. A flange extends radially from the open proximal end of the receptacle to engage an interior surface of the projection. The receptacle includes dimensions sufficient to provide a fluid tight seal between the projection and base portion channel to maintain fluid within the channel.

Temperature probe 98 is disposed within the device housing and extends through opening 75 defined in the base plate to be removably inserted within the receptacle when the cassette is placed on the base plate. The distal end of the probe is disposed in contact with the receptacle closed end, while the probe may be secured within the receptacle via friction fit, a locking or securing mechanism or any other securing techniques. Cassette 50 is placed on the heater plate with projection 94 inserted within the base plate opening 75 to enable the probe to engage the receptacle. Sensor wiring (not shown) connects the probe to controller 62 (FIGS. 2) to provide a fluid temperature for controlling system operation. The receptacle is typically sterile and permits re-use of temperature probe 98 with subsequent cassettes to maintain sterility. The temperature probe may be implemented by any conventional or other temperature sensor (e.g., RTD, IR, NTC, thermistor, thermocouple, etc.). The fitting may be substantially similar to the temperature sensing device disclosed in co-pending U.S. patent application Ser. No. 09/973,988, entitled "Temperature Sensing Device for Selectively Measuring Temperature at Desired Locations Along an Intravenous Fluid Line" and filed on Oct. 11, 2001, the disclosure of which is incorporated herein by reference in its entirety.

Controller 62 (FIG. 2) has a generally rectangular configuration with suitable dimensions to permit insertion of the controller into opening 13 defined in the housing front wall. The controller includes a front panel 64 including dimensions slightly greater than opening 13 to allow the front panel to remain external of the housing and accessible to a user. Front panel 64 includes a display 66 (e.g., LED, LCD, etc.) and input devices 67 (e.g., buttons, keys, etc.) that enable entry of a desired or set point temperature for the fluid or other information (e.g., entering desired fluid heating temperatures, controls for various threshold heater plate temperatures, etc.) to direct controller operations. The set point temperature may alternatively be predetermined or pre-programmed into the controller for device operation.

The controller display may provide various information to an operator (e.g., whether or not the tubing cassette is properly aligned on the base plate to permit heating, utilization of an incompatible cassette with the device, desired or set point temperature information, temperatures measured by temperature sensors disposed within the device, excessive temperature measurements, etc.). Alternatively, the housing may include various visual and/or audible indicators (e.g., LED's, audio, speech, etc.) to indicate various conditions (e.g., proper placement of the cassette within the device, excessive temperatures, incompatible cassette being employed with the device, device ready for operation, etc.). Further, the controller may provide variable controls to control device operation in response to various temperature measurements (e.g., output fluid temperature, cassette temperature, heating element temperatures, heater plate temperature and/or resistance, IV solution bag or container temperature, serpentine tubing section temperature, etc.). The controller may further provide measured temperature information to an external display or a printer, and may record the number of heating sessions conducted by the device by accumulating the quantity of cover closures and/or heating element enablements. The controller may provide this information, typically in the form of a count, to the operator.

The cover and heater plate heating elements are controlled by the controller utilizing feedback from temperature sensors and/or probes disposed within the housing in proximity to the heater plate and the tubing cassette. The controller basically provides resistive control of the heating elements disposed on the cover and heater plate (e.g., adjusts power or current to these heating elements), and may control these heating elements based on a resistance measurement of the heater plate, or based on the heater plate and/or fluid temperatures. Further, the warming device may include a plurality of sensors to monitor the heating elements, heater plate and/or cassette to provide various safeguards for device operation (e.g., disable the device in response to excessive temperature measurements, etc.). The temperature sensors are preferably implemented by conventional RTD temperature sensors, and are preferably employed to measure the temperature of the heater plate and fluid flowing within the tubing cassette. However, the temperature sensors may be implemented by any conventional or other type of temperature sensor (e.g., NTC, IR, thermocouple, thermistors, etc.) and may measure any device component or fluid temperature. A heater plate temperature sensor 84 (FIG. 5) may be disposed at any suitable location on or in close proximity to the heater plate for direct or indirect temperature measurement. Similarly, a fluid temperature sensor may be disposed at any suitable location on or within the tubing cassette for direct or indirect temperature measurement of the fluid flowing therein.

Figure 5:
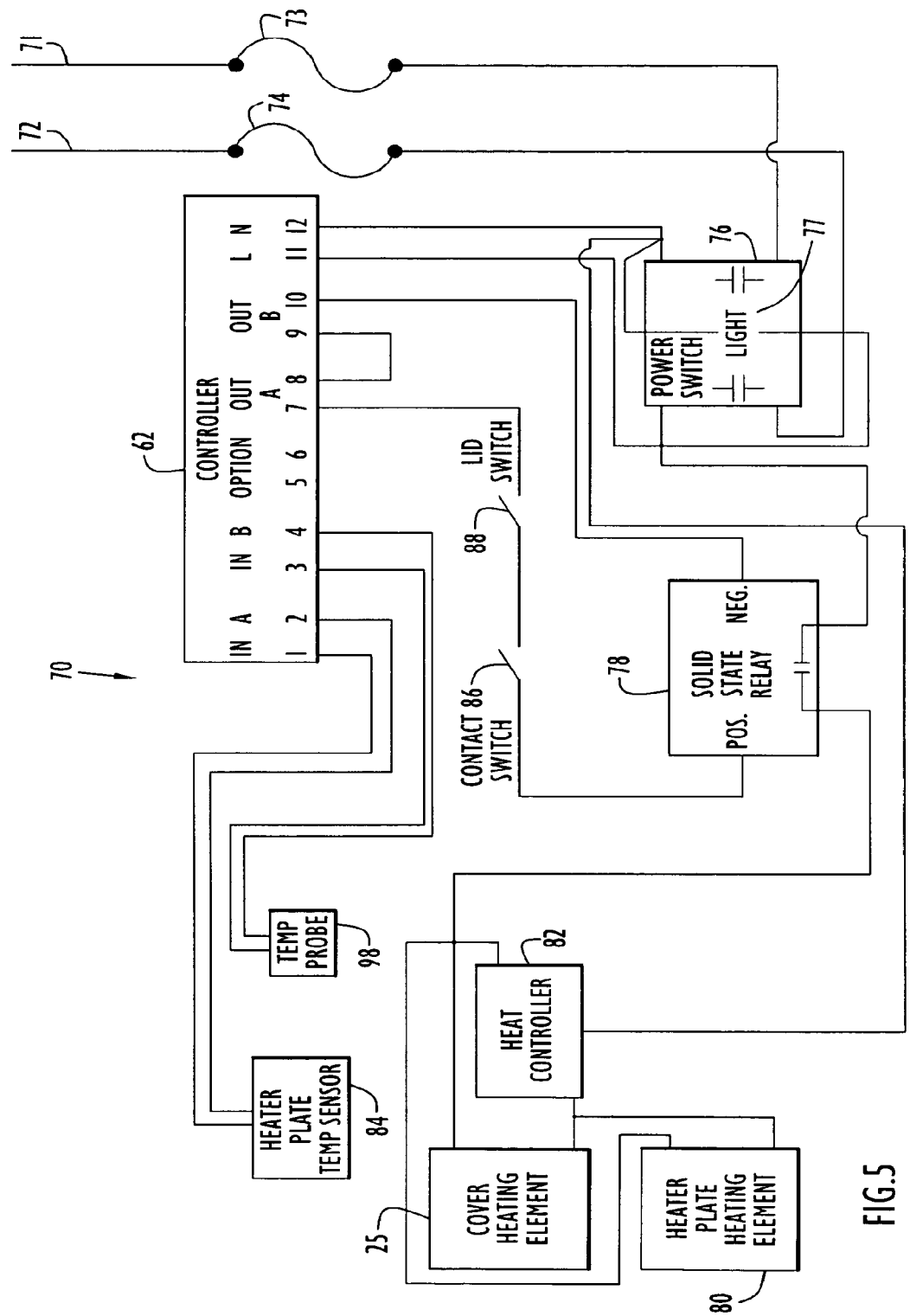
FIG. 5 is an electrical schematic diagram of an exemplary control circuit for the warming device of FIG. 1.

An exemplary control circuit to facilitate control of device operation is illustrated in FIG. 5. Specifically, control circuit 70 includes power conductors 71, 72, a power switch 76, a solid state relay 78, heater plate heating element 80, cover heating element 25, a heat controller 82, heater plate temperature sensor 84, temperature probe 98 and controller 62. The relay and heat control components (e.g., relay 78 and controllers 62, 82) and corresponding electrical connections may be housed on a printed circuit board disposed within the device housing. Power conductors 71, 72 each include a respective fuse 73, 74 that is arranged in series with power switch 76 to prevent power surges from damaging the switch and circuitry. The conductors receive power from an external power source, preferably in the form of batteries. However, any suitable internal or external power source may be utilized (e.g., AC, DC, wall outlet jack, batteries, etc.). Power may further be received from an infusion pump or device, such as the device disclosed in U.S. patent application Ser. No. 09/380,507, entitled "Method and Apparatus for Pressure Infusion and Temperature Control of Infused Liquids" and filed on Sep. 3, 1999, the disclosure of which is incorporated herein by reference in its entirety. Power switch 76 controls power to the circuitry and is connected to controller 62, relay 78 and heat controller 82. The power switch may include a light 77 to illuminate the switch. Controller 62 is further connected to relay 78 and temperature sensors 84, 98, while heat controller 82 is further connected to relay 78 and heating elements 25, 80. The heat controller controls power to both heating elements to enable those elements to achieve and maintain a predetermined temperature (e.g., a temperature generally sightly greater than a desired fluid temperature). Controller 62 controls power to heat controller 82, via relay 78, based upon a comparison of a preset or desired temperature with temperatures of the heater plate and fluid within cassette 50 measured by temperature sensors 84, 98, respectively. In particular, controller 62 receives temperature signals from heater plate temperature sensor 84 and temperature probe 98 indicating the temperatures of the heater plate and IV fluid flowing within the tubing cassette. In response to either temperature measured by sensors 84, 98 being equal to or exceeding the desired temperature, controller 62 disables power to heat controller 82, thereby disabling heating elements 25, 80. Conversely, when either of the temperatures measured by sensors 84, 98 are below the desired temperature, controller 62 enables power to the heat controller to energize those heating elements. Controller 62 basically serves as a safety monitor to control device operation in response to fluid and/or heating element temperatures. Further, controller 62 may disable the heating elements in response to detection of the absence of fluid within the cassette or detection of the presence of air bubbles within the fluid. The fluid detection may be performed by a fluid sensor disposed within the warming device, or by temperature probe 98 providing a temperature measurement within a particular range or below a certain threshold. The air bubbles may be detected by an ultrasonic air detector to enable cessation of fluid flow prior to air bubbles reaching a patient and causing injury.

Switches 86, 88 are connected in series between controller 62 and relay 78. Switch 86 represents the connection between contact 60 (FIG. 2) of tubing cassette 50 with conductive post 40 of base plate 30 and contact 26 of cover heating element 25, while switch 88 represents a switch to enable device operation when the cover is in a closed state. The switches basically permit relay 78 to be enabled by controller 62 in response to proper alignment of the tubing cassette on the base plate (e.g., the formation of the electrical path further serves to indicate the presence of a cassette compatible with the warming device) and closing of the cover. Thus, the switches enable device operation and control of the cover and heater plate heating elements by controller 62 during the presence of those conditions, and effectively disables the heating elements during absence of the conditions (e.g., the switches disable the heating elements in response to employment of an incompatible cassette, misalignment of the cassette on the base plate or the cover residing in an open state).

Operation of the IV line temperature controlled warming device is described with reference to FIGS. 1-5. Initially, an operator pivots cover 22 to an open position for insertion of IV tubing cassette 50 between the base plate and the cover. The tubing cassette is inserted within the device with cassette body 57 aligned with annular groove 36, inlet and outlet portions 52, 54 and serpentine tubing section 56 respectively aligned with channels 37, 38 and fitting projection 94 disposed within base plate opening 75 to receive temperature probe 98 within fitting projection receptacle 96. Upon proper insertion of the cassette into the warming device, contact member 60 contacts conductive post 40 and contact 26 of the cover heating element to enable device operation. The operator subsequently pivots the cover to a closed position and secures the latching mechanism on the cover with the housing to ensure contact between tubing cassette contact 60, conductive post 40 and cover heating element contact 26. The controller may indicate on display 66 proper securement of the tubing cassette within the base plate as described above, and may further indicate that the heating elements are enabled (i.e., switches 86, 88 are closed) to heat the tubing cassette. Inlet and outlet terminals 53, 55 of the tubing cassette are connected to portions of an IV line that extends between an IV fluid supply source (e.g., an IV solution bag or container) to an infusion site on a patient.

The operator may enter a desired temperature for the IV fluid flowing within the tubing cassette via the input devices on the controller front panel. Heat controller 82 controls the heating elements of the heater plate and the cover to attain a predetermined temperature, while controller 62 controls power to the heat controller, via relay 78, based upon measured temperatures provided by the heater plate temperature sensor and temperature probe. Thus, the warming device of the present invention enables fluid flowing within the tubing cassette to achieve and maintain a desired fluid temperature. The configuration of the cassette is also advantageous in that it provides a long residence time for fluid flowing therein, thereby ensuring that fluid exiting the cassette attains the desired temperature. The concentric configuration of the tubing cassette portions further provides enhanced heat exchange between fluid within adjacent concentric tubing sections. Upon completion of a heating session, the cover may be opened, and the tubing cassette removed and discarded. A new and sterile tubing cassette may then be inserted into the housing for use in another heating application. The controller may further record the number of heating sessions conducted with the warming device by counting the number of times the cover is closed (e.g., a tubing cassette is inserted within the housing and the cover is closed) and/or the heating elements are enabled. The controller may provide count information to the operator relating to the number of times the warming device has been utilized.

Figure 6:
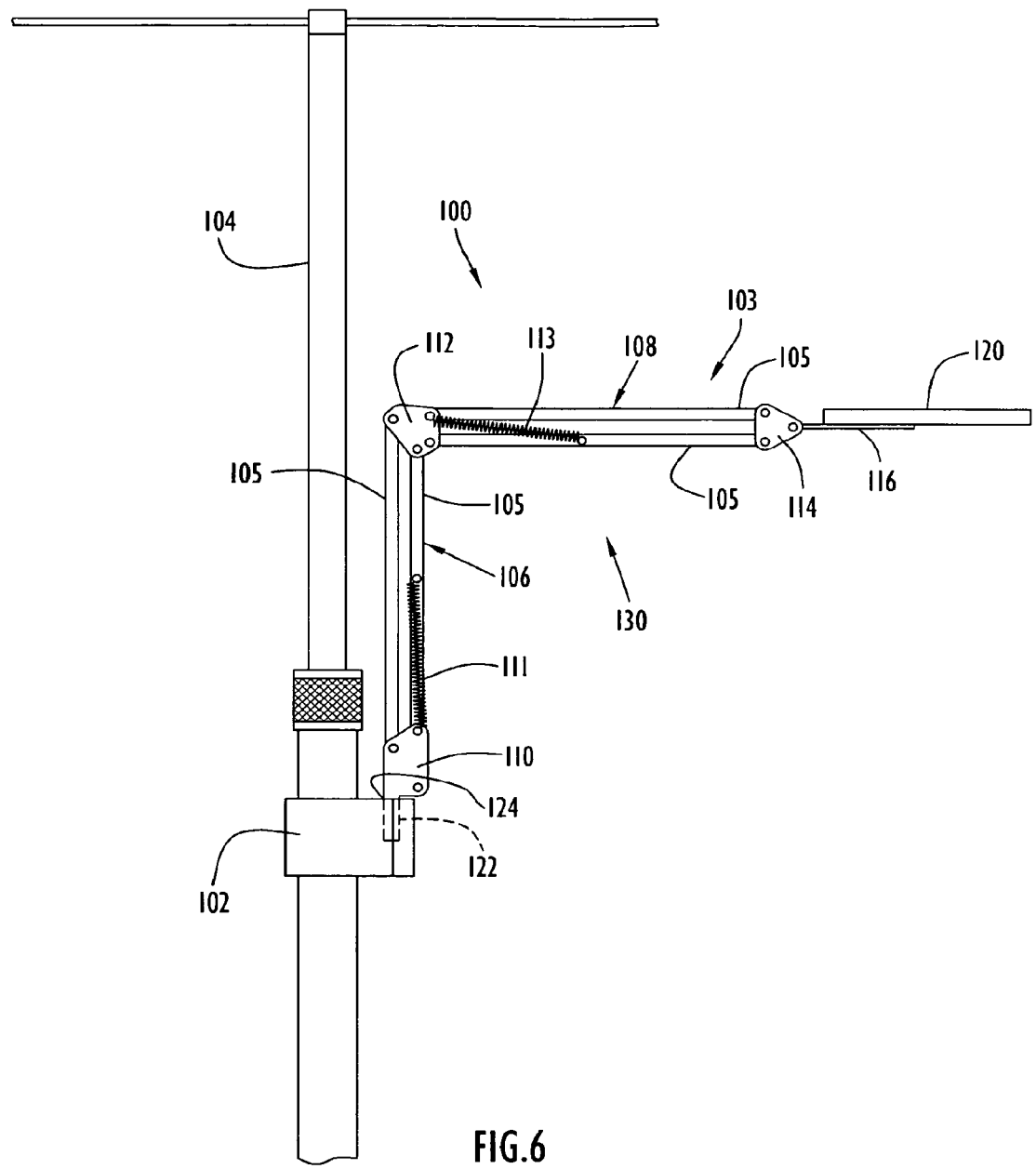
FIG. 6 is a side view in perspective of a mount utilized to support a warming device according to the present invention.

An exemplary pole type mount for use with the IV line warming device is illustrated in FIG. 6. Specifically, mount 100 includes an arm 103 and a swivel connector 102 (e.g., a manipulable bracket) securable around a portion of an IV pole 104 to attach the arm to the pole. Arm 103 is secured to connector 102 and includes a lower arm section 106 and an upper arm section 108. Each arm section includes a pair of generally cylindrical rods 105 extending substantially parallel to each other and secured at each end to respective pivot mounts as described below. Lower arm section 106 is pivotally secured at a proximal end to a proximal pivot mount or bracket 110 and at a distal end to an intermediate pivot mount or bracket 112. Proximal pivot mount 110 includes a substantially cylindrical projection 122 that is received within a channel 124 defined in connector 102. The projection and channel rotatably secure proximal pivot mount 110 to connector 102, while a proximal helical spring 111 is secured at one end to proximal pivot mount 110 and at the other end to a rod 105 of lower arm section 106. Upper arm section 108 is pivotally secured at a proximal end to intermediate pivot mount 112 and at a distal end to a distal device mount or bracket 114. A base plate 116 is attached to the distal device mount, while a platform or tray 120 is attached to the base plate top surface to support an item, such as the warming device. The tray may be manipulable relative to the distal device mount for enhanced positioning of an item. A distal helical spring 113 is secured at one end to intermediate pivot mount 112 and at the other end to a rod 105 of upper arm section 108. The connections between the rods and pivot mounts permit pivoting of the lower and upper arm sections relative to each other and to pole 104, thereby facilitating placement of the warming device at a variety of locations with respect to the IV pole.

It will be appreciated that the embodiments described above and illustrated in the figures represent only a few of the many ways of implementing a method and apparatus for heating solutions within intravenous lines to desired temperatures during infusion.

The warming device may be of any shape or size, may be positioned at any desired locations in any orientation, and may heat any types of medical or other fluids. The device housing may be of any shape or size and may be constructed of any suitable materials. The housing materials are preferably transparent to enable viewing of the fluid and any conditions within the device (e.g., contamination, air bubbles, etc.), but may have any degree of transparency (e.g., transparent, translucent, opaque, etc.). The housing walls may be of any quantity, shape or size and may be constructed of any suitable materials. The controller may be disposed at any suitable location on or within the housing, while the housing opening may be of any shape or size and be defined at any suitable location on the housing to receive the controller. The housing interior may include any suitable configuration to partially or completely receive any quantity of controllers, base plates, heater plates, IV tubing cassettes or other device components. For example, the housing may be configured for receiving a plurality of tubing cassettes in order to heat fluid within plural separate IV fluid lines. The device components may be arranged in any fashion within the housing.

The base plate may be of any quantity, shape or size, may include any suitable configuration and may be constructed of any suitable materials. The base plate is preferably transparent to enable viewing of the fluid as described above, but may have any degree of transparency (e.g., transparent, translucent, opaque, etc.). The base plate may be secured at any suitable location on or within the housing. The base plate lower and upper portions may be of any quantity, shape or size, while the base plate may be secured to the housing via any securing techniques (e.g., friction fit, brackets, etc.). The base plate surface may include any quantity of grooves and/or channels having any suitable configuration for receiving and retaining the heater plate and cassette. The annular groove and tangential channel may be of any shape or size and may be defined at any suitable locations within the base plate. Alternatively, the base plate may include securing mechanisms (e.g., hooks, clasps, etc.) to secure the cassette to the base plate. The engagement section may be of any quantity, shape or size and may be defined at any suitable locations on the base plate. The serpentine channel may be of any quantity, shape or size, and may be defined in the engagement section or base plate at any suitable locations. The serpentine channel may include any pattern or configuration (e.g., spiral, zig-zag, linear, etc.). The temperature probe opening may be of any quantity, shape or size, and may be defined at any suitable locations within the base plate. The conductive post may be of any quantity, shape or size, may be disposed at any suitable location within the serpentine channel or on the base plate, and may be constructed of any suitable conductive materials.

The heater plate may be of any quantity, shape or size, and may be constructed of any suitable thermally conductive materials. The heater plate may include any suitable configuration for being received and retained by the base plate and for heating the tubing cassette. The plate annular portion and projections may be of any shape or size, while the projections may be disposed at any suitable locations. The heater plate may include a grooved or other type of surface to receive cassette tubing sections or to form fluid flow paths to enable use of the device without the cassette. The heater plate may include any quantity of any type of conventional or other heating element secured to the plate at any desired locations via any securing techniques (e.g., bracket, adhesives, etc.). The heater plate may include any quantity of temperature or other sensors disposed at any suitable locations on or proximate the heater plate to measure heater plate temperature and/or resistance.

The tubing cassette may be of any quantity, shape or size and may be constructed of any suitable materials. The cassette may include any suitable configuration for being received and retained by the base plate. The inlet and outlet tubing portions of the cassette may include any suitable connector for securing those portions to any desired sections of an IV line. The outlet portion may alternatively direct heated fluid from the cassette to any desired location (e.g., an infusion or other site, a storage container, etc.). The cassette may include any type of tubing or other materials suitable to define a flow path for fluid. The cassette may include any quantity of tubing sections arranged in any desired manner (e.g., concentric, serpentine, zig-zag, linear, spiral, nested, etc.) to provide sufficient residence time for fluid within the device, wherein fluid flow directions within the sections may be arranged in any desired pattern or fashion. The cassette may include any quantity of concentric tubing sections, while the serpentine section may include any configuration (e.g., serpentine, circular, linear, spiral, etc.) that reverses fluid flow within the cassette. The serpentine section may be disposed at any location within the fluid flow path. The warming device may accommodate any quantity of cassettes, while the cassette may include any quantity of tubing section layers (e.g., any quantity of tubing sections on any quantity of planes (e.g., each stacked above or adjacent the other, etc.)). The cassette may include any suitable structures to form the fluid flow path (e.g., tubing, sealed channels, pools, chambers, etc.). The inlet and outlet portions may be used in any fashion to enable fluid to flow into and out of the cassette.

The cassette backing may be of any quantity, shape or size, may receive the cassette at any suitable locations, and may be constructed of any suitable materials. The backing may include any configuration enabling access to the conductive post and contacts. The backing may include any quantity of tabs of any shape or size and disposed at any suitable locations. The tabs may be constructed of any suitable materials. The cassette contact may be of any quantity, shape or size, may be disposed at any suitable locations on the serpentine section or cassette, and may be constructed of any suitable conductive materials. The electrical path may be formed through any device components, where contacts may be disposed on any quantity of any device components at any suitable locations. The formation of the electrical path may be utilized to indicate any types of conditions (e.g., open cover, presence of fluid, placement of cassette, etc.). The electrical path may include a pressure switch to sense closure of the cover, where the pressure switch may include a dual sensor element to further sense temperature.

The housing cover may be of any quantity, shape or size, and may be constructed of any suitable materials. The cover is preferable transparent to enable viewing of the fluid as described above, but may have any degree of transparency (e.g., transparent, translucent, opaque, etc.). The cover may be secured to the housing or base plate in any manner, and may include any quantity of any type of handle or other structure of any shape or size and disposed at any suitable location to facilitate manipulation of the cover. The latching mechanism may be any type of conventional or other securing device (e.g., hook and clasp, engaging members, etc.) for securing the cover to the housing and/or base plate, and may be disposed at any suitable locations on the housing, base plate and/or cover. The cover may include any quantity of any type of conventional or other heating device (e.g., heating pad, acrylic heater, coils, etc.). The heating element wiring may be embedded within or disposed on the sheet in any fashion and include any configuration suitable to heat the cassette. The heating element contact may be of any quantity, shape or size, may be disposed within or on the sheet at any suitable locations and may be constructed of any conductive materials. The terminals may be of any quantity, shape or size, and may be embedded within or disposed on the sheet at any suitable locations.

The fitting may be of any quantity, shape or size, may be constructed of any suitable materials and may be disposed at any suitable locations along the IV line or cassette. The fitting base and projection may be of any quantity, shape or size and may be constructed of any suitable materials. The base channel may be of any shape or size, may be defined in the base at any locations and extend in any desired directions. The fluid line or cassette may be secured to the fitting via any conventional or other locks or connectors. The base and projection may be arranged or connected in any fashion, while the fitting may have any suitable configuration (e.g., T-type fitting, Y-type fitting, cross fitting, coupling, etc.). The fitting may be included within and permanently or releasably connected to the cassette or a disposable IV line set. The fitting may include a receptacle to maintain fluid sterility and permit re-use of the temperature probe. The receptacle may be of any quantity, shape or size, may be constructed of any suitably thermally conductive materials and may be disposed at any locations within the projection or fitting suitable to contact or thermally conduct heat from fluid flowing within the fitting. The receptacle body and flange may be of any quantity, shape or size and may be constructed of any suitable materials. The temperature probe may be inserted and secured within the base plate opening and receptacle via any conventional or other securing techniques (e.g., friction fit, threaded engagement, securing mechanism, etc.). Similarly, the receptacle may be secured within the projection or fitting via any conventional or other securing techniques (e.g., friction fit, adhesives, threaded engagement, securing mechanism, etc.). The fitting may alternatively include the temperature probe embedded therein.

The temperature sensors or probes of the warming device may be of any quantity and may be disposed at any suitable locations within or on the device or device components (e.g., base plate, heater plate, cassette, housing, etc.) to measure any desired temperatures. The temperature sensors or probes may be implemented by any quantity of any type of conventional or other temperature measuring devices (e.g., RTD, IR, NTC, thermistors, thermocouples, etc.). The sensors or probes may be of any shape or size to accommodate a particular application.

The controller may be implemented by any quantity of any conventional or other microprocessor, controller or circuitry. The controller may be disposed at any suitable location on or within the housing or separate from the device (e.g., wireless or other communication link to components, etc.). The controller may include any quantity of any type of display (e.g., LED, LCD, etc.) or indicators (e.g., visual, audio, speech synthesis, etc.) disposed at any suitable locations to convey any desired information or conditions to an operator (e.g., desired temperatures, measured temperatures, improper placement of cassette within device, etc.). The controller may include any quantity of any type of input devices (e.g., buttons, keys, voice recognition, etc.) to receive information.

The fluid temperature may be predetermined or entered by a user, where the device typically heats fluid to temperatures in the approximate range of 60° F.-160° F. However, the device may be utilized to heat and/or cool fluid (e.g., by employing cooling or refrigeration devices instead of or in conjunction with the heating elements) to any desired temperature or temperature range. The controller may be coupled to any quantity of external displays or printing devices to display and/or print any desired information. The controller may further control device operation in response to any measured conditions (e.g., fluid flow, various temperatures, contamination, air bubbles, etc.). The warming device may employ any quantity of any type of sensors (e.g., flow sensors, fluid sensors to detect fluid, temperature sensors, resistive sensors, ultrasonic air detectors or other sensors to detect air bubbles, etc.) to measure and/or detect conditions to control device operation.

The controller may record and facilitate display of device utilization information (e.g., the amount of time of device use, quantity of times the cover has been closed, the quantity of times of heater enablement, etc.). The controller may receive any quantity of inputs and control any quantity of warming devices, and may utilize any conventional or other control algorithms (e.g., fuzzy logic, PID, etc.).

The heat controller may be implemented by any quantity of any conventional or other microprocessor, controller or circuitry. The heat controller may control the heating elements to any desired temperature or temperature range, but preferably controls the heating elements to temperatures slightly above the desired range for the application. The heat controller may receive any quantity of inputs and control any quantity of heating elements, and may utilize any conventional or other control algorithms (e.g., fuzzy logic, PID, etc.). The device may employ the controller to directly control the heating elements without the heat controller. The controllers are each typically implemented by a commercially available controller pre-programmed and loaded with its own software, but may be implemented by any quantity of any conventional or other type of controller, microprocessor, or circuitry capable of controlling the warming device.

The control circuit components (e.g., power switch, relay, fuses, controllers, etc.) maybe implemented by any quantity of any conventional or other electrical components arranged in any fashion and performing the functions described above. The circuit may be disposed at any location on the or within the housing and may be arranged in any fashion to control device operation as described above. The fuses may be implemented by any conventional or other fuses or limiting devices configured for any desired current level. The power switch and controllers may be disposed at any suitable locations on or within the housings. The printed circuit board may include any quantity of any circuit components, while the control circuit may receive power from any suitable power source (e.g., AC, DC, wall outlet jack, batteries, infusion device, etc.). The control circuit may be modified in any fashion and include any components to perform the functions described herein. The switches may be implemented by any conventional or other switching devices to enable or disable device operation in response to any desired conditions.

The warming device may be supported in various positions and orientations by any suitable structures (e.g., a patient arm or other body portion, swing arm, arm board, bed, bed rail, operating room or other table, IV pole, wall, floor, posts, etc.). The warming device is preferably positioned in close proximity to an infusion site of a patient in order to heat IV fluid (e.g., may heat fluid with or without skin contact), but may be used at any desired location along an IV line. The warming device may be utilized for operating room, pre-op and/or post-op procedures or at any other times where infusion is being performed. The mount may be of any shape or size, and may be constructed of any suitable materials. An IV pole or other structure may support any quantity of mounts and/or warming devices. The mount components (e.g., pivot mount, connectors, springs, rods, base plate, tray, etc.) may be of any quantity, shape or size, may be constructed of any suitable materials and may be disposed or connected at any suitable locations in any desired orientation or manner relative to each other (e.g., the rods may be parallel to each other or arranged in any fashion, the tray may be connected to the base plate at any location, etc.). The components may be connected via any suitable securing techniques (e.g., bolts, integrated, hooks, etc.), and may be arranged and/or connected to each other in any fashion. Further, the mount components may be implemented by any conventional or other components performing the functions described herein. The projection may be of any quantity, shape or size, while the channel may be of any quantity, shape or size and defined in the connector at any suitable location. The arm may alternatively be connected to the connector via any conventional or other securing techniques (e.g., bracket, hinge, etc.).

From the foregoing description, it will be appreciated that the invention makes available a novel method and apparatus for heating solutions within intravenous lines to desired temperatures during infusion, wherein a warming device receives and heats a preformed IV tubing cassette or cartridge connected to an IV line to warm solution flowing within the line to a desired temperature during infusion into a patient.

Having described preferred embodiments of a new and improved method and apparatus for heating solutions within intravenous lines to desired temperatures during infusion, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A fluid cassette to receive fluid from a fluid line and facilitate heating of said fluid to a desired fluid temperature within an intravenous fluid warming device having a base plate and a lid, said fluid cassette comprising:
    an elongated portion of flexible tubing constructed from an intravenous fluid line and including an inlet tubing portion with an inlet terminal to receive fluid into said fluid cassette from said fluid line and an outlet tubing portion with an outlet terminal to release fluid from said fluid cassette to said fluid line; and
    a conductive contact encircling a substantially central portion of said flexible tubing and completing an electrical connection between the lid and the base plate when the lid is in a closed position to indicate a presence of said fluid cassette within the intravenous fluid warming device and control device operation;
    wherein said elongated portion of flexible tubing is manipulated to form and maintain a spiral portion including a plurality of nested tubing sections in fluid communication with said inlet and outlet tubing portions and arranged adjacent each other, each said tubing section defining a path for said fluid from said fluid line to flow in a particular direction, and wherein said fluid flow direction within each tubing section is opposite the fluid flow direction within each tubing section adjacent that section.

2. The fluid cassette of claim 1, wherein said tubing sections are concentric and define a fluid cassette annular section, and said inlet and said outlet tubing portions extend tangentially from said annular section.

3. The fluid cassette of claim 2, wherein said annular section includes an intermediate section to direct fluid flow received from said inlet terminal in a reverse direction through said annular section toward said outlet terminal.

4. The fluid cassette of claim 1, further including a fitting disposed within said outlet tubing portion toward said outlet terminal and in fluid communication with said flexible tubing to permit fluid to flow within said fitting, wherein said fitting receives a temperature sensor to measure temperature of said fluid flowing within said fluid cassette.

5. The fluid cassette of claim 4, wherein said fitting includes a thermally conductive member disposed within said fitting and in direct contact with fluid flowing through said fitting, wherein said thermally conductive member receives said temperature sensor to measure temperature of said fluid flowing within said fluid cassette.

6. The fluid cassette of claim 1, further including at least one engagement member to facilitate manipulation, insertion and removal of said fluid cassette within said intravenous fluid warming device.

7. A method of heating intravenous fluids to desired temperatures within an intravenous fluid warming device having a base plate and a lid comprising:
    forming a fluid cassette for said intravenous fluid warming device by manipulating an elongated portion of flexible tubing constructed from an intravenous fluid line to form and maintain a spiral portion including a plurality of nested tubing sections in fluid communication with inlet and outlet tubing portions and arranged adjacent each other, each said tubing section defining a path for said fluid from a fluid line to flow in a particular direction, and wherein said fluid flow direction within each tubing section is opposite the fluid flow direction within each tubing section adjacent that section; and
    providing a conductive contact which encircles a substantially central portion of said flexible tubing, wherein said conductive contact completes an electrical connection between the lid and the base plate when the lid is in a closed position to indicate a presence of said fluid cassette within the intravenous fluid warming device and control device operation;
    wherein said inlet tubing portion includes an inlet terminal to receive fluid into said fluid cassette from said fluid line and said outlet tubing portion includes an outlet terminal to release fluid from said fluid cassette to said fluid line.

8. The method of claim 7, wherein said tubing sections are concentric and define a fluid cassette annular section, and said inlet and said outlet tubing portions extend tangentially from said annular section.

9. The method of claim 8, wherein said annular section includes an intermediate section to direct fluid flow received from said inlet terminal in a reverse direction through said annular section tubing sections toward said outlet terminal.

10. The method of claim 7, wherein said fluid cassette further includes a fitting disposed within said outlet tubing portion toward said outlet terminal and in fluid communication with said flexible tubing to permit fluid to flow within said fitting, wherein said fitting receives a temperature sensor to measure temperature of said fluid flowing within said fluid cassette.

11. The method of claim 10, wherein said fitting includes a thermally conductive member disposed within said fitting for direct contact with fluid flowing through said fitting, said thermally conductive member for receiving said temperature sensor to measure temperature of said fluid flowing within said fluid cassette.

12. The method of claim 7, further including:
at least one engagement member coupled to said fluid cassette to facilitate manipulation, insertion and removal of said fluid cassette within said intravenous fluid warming device.

* * * * *